(12) United States Patent
Shuttleworth et al.

(10) Patent No.: US 9,200,007 B2
(45) Date of Patent: Dec. 1, 2015

(54) TRICYCLIC HETEROCYCLIC COMPOUNDS AS PHOSPHOINOSITIDE 3-KINASE INHIBITORS

(75) Inventors: Stephen Joseph Shuttleworth, Hampshire (GB); Alexander Richard Liam Cecil, Hampshire (GB); Thomas James Hill, Hampshire (GB); Franck Alexandre Silva, Hampshire (GB)

(73) Assignee: Karus Therapeutics Limited, Southampton (GB)

( * ) Notice: Subject to any disclaimer, the term of this patent is extended or adjusted under 35 U.S.C. 154(b) by 62 days.

(21) Appl. No.: 13/388,164

(22) PCT Filed: Aug. 19, 2010

(86) PCT No.: PCT/GB2010/051370
§ 371 (c)(1),
(2), (4) Date: Mar. 27, 2012

(87) PCT Pub. No.: WO2011/021038
PCT Pub. Date: Feb. 24, 2011

(65) Prior Publication Data
US 2012/0178737 A1 Jul. 12, 2012

(30) Foreign Application Priority Data

Aug. 20, 2009 (GB) .................................. 0914594.7
Apr. 1, 2010 (GB) .................................. 1005584.6

(51) Int. Cl.
C07D 491/147 (2006.01)
C07D 495/14 (2006.01)
C07D 519/00 (2006.01)

(52) U.S. Cl.
CPC .......... *C07D 495/14* (2013.01); *C07D 491/147* (2013.01); *C07D 519/00* (2013.01)

(58) Field of Classification Search
CPC .......................... C07D 491/147; C07D 495/14
USPC ......................................... 544/115; 514/232.8
See application file for complete search history.

(56) References Cited

U.S. PATENT DOCUMENTS

| | | |
|---|---|---|
| 2002/0151544 A1 | 10/2002 | Hayakawa et al. |
| 2013/0109688 A1 | 5/2013 | Shuttleworth et al. |

FOREIGN PATENT DOCUMENTS

| | | |
|---|---|---|
| EP | 1 277 738 A1 | 1/2003 |
| WO | WO 01/83456 A1 | 8/2001 |
| WO | WO 2007/122410 A1 | 11/2007 |
| WO | WO 2007/127183 A1 | 11/2007 |
| WO | WO 2010/052569 A2 | 5/2010 |
| WO | WO-2013-132270 A1 | 9/2013 |

OTHER PUBLICATIONS

Hayakawa, et al., "Synthesis and Biological Evaluation of Pyrido[3',2':4,5]furo[3,2-*d*]pyrimidine Derivatives as Novel PI3 Kinase p110αInhibitors" *Bioorganic & Medicinal Chemistry Letters*, 2007, vol. 17, pp. 2438-2442.

*Primary Examiner* — Rebecca Anderson
(74) *Attorney, Agent, or Firm* — Goodwin Procter LLP

(57) ABSTRACT

Compounds of formula (I) or a pharmaceutically acceptable salt thereof, wherein: W is O, N—H, N-($C_1$-$C_{10}$ alkyl) or S; each X is independently CH or N; $R^1$ is a 5 to 7-membered saturated or unsaturated, optionally substituted heterocycle containing at least 1 heteroatom selected from N or O; $R^2$ is (LQ)$_m$Y; and each $R^3$ is independently H, $C_1$-$C_{10}$ alkyl, aryl or heteroaryl, are surprisingly found to be inhibitors of PI3K-p110δ, and therefore have utility in therapy.

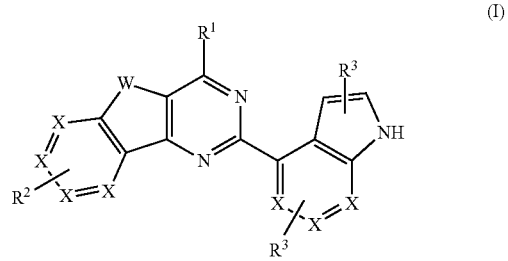

6 Claims, No Drawings

TRICYCLIC HETEROCYCLIC COMPOUNDS AS PHOSPHOINOSITIDE 3-KINASE INHIBITORS

CROSS REFERENCE TO A RELATED APPLICATION

This application is a National Stage Application of International Application Number PCT/GB2010/051370, filed Aug. 19, 2010; which claims priority to Great Britain Application Nos. 0914594.7, filed Aug. 20, 2009 and 1005584.6, filed Apr. 1, 2010.

FIELD OF THE INVENTION

The present invention relates to novel compounds which act as inhibitors of the class IA phosphoinositide 3-kinase enzyme, PI3K-p110δ, for the treatment of cancer, immune and inflammatory diseases.

BACKGROUND OF THE INVENTION

The phosphoinositide 3-kinases (PI3Ks) constitute a family of lipid kinases involved in the regulation of a network of signal transduction pathways that control a range of cellular processes. PI3Ks are classified into three distinct subfamilies, named class 1. H, and HI based upon their substrate specificities. Class IA PI3Ks possess a p110α, p110β, or p110δ catalytic subunit complexed with one of three regulatory subunits, p85α, p85β or p55δ. Class IA PI3Ks are activated by receptor tyrosine kinases, antigen receptors, G-protein coupled receptors (GPCRs), and cytokine receptors. The class IA PI3Ks primarily generate phosphatidylinositol-3,4,5-triphosphate (PI(3,4,5)P$_3$), a second messenger that activates the downstream target AKT. The consequences of biological activation of AKT include tumour cell progression, proliferation, survival and growth, and there is significant evidence suggesting that the PI3K/AKT pathway is dysregulated in many human cancers. Additionally. PI3K activity has been implicated in endocrinology, cardiovascular disease, immune disorders and inflammation. It has been established that PI3K-p110δ plays a critical role in the recruitment and activation of immune and inflammatory cells. PI3K-p110δ is also upregulated in a number of human tumours and plays a key role in tumour cell proliferation and survival.

Compounds which are able to modulate p110δ activity have important therapeutic potential in cancer and immune and inflammatory disorders.

WO2006/046035 describes fused pyrimidines, which have activity as inhibitors of PI3K. The compounds disclosed therein exhibit selectivity for class Ia PI3Ks, notably p110δ.

SUMMARY OF THE INVENTION

The present invention is a compound of formula I:

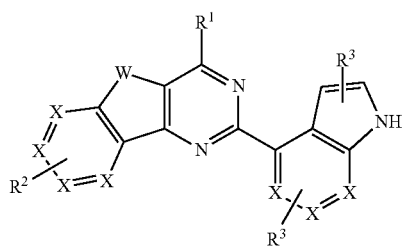

(I)

or a pharmaceutically acceptable salt thereof, wherein:
W is O, N—H, N—(C$_1$-C$_{10}$ alkyl) or S;
each X is independently CH or N;
R$^1$ is a 5 to 7-membered saturated or unsaturated, optionally substituted heterocycle containing at least 1 heteroatom selected from N or O;
R$^2$ is (LQ)$_m$Y;
each L is independently a direct bond, C$_1$-C$_{10}$ alkylene, C$_2$-C$_{10}$ alkenylene, C$_2$-C$_{10}$ alkynylene, arylene or C$_3$-C$_{10}$ cycloalkylene;
each Q is independently a direct bond, heteroarylene, a heterocycle linker, —O—, —NR$^3$—, —C(O)—, —C(O)NR$_3$—, —SO$_2$—, —SO$_2$—NR$^3$—, —N—C(O)—NR$^3$—, —N—SO$_2$—NR$^3$, halogen, —C(halogen)$_a$(R$^3_{(2-a)}$)—, —NR$^4$R$^5$—, —C(O)NR$^4$R$^5$, where R$^4$ and R$^5$ together with the nitrogen to which they are attached form a 5 to 7-membered heterocycle linker;
m is from 0 to 5;
Y is H, C$_1$-C$_{10}$ alkyl, C$_2$-C$_{10}$ alkenyl, C$_2$-C$_{10}$ alkenyl, C$_2$-C$_{10}$ alkynyl, aryl, C$_3$-C$_{10}$ cycloalkyl, heterocycle, heteroaryl, —OR$^3$, —N(R$^3$)$_2$, —C(O)R$^3$, —C(O)OR$_3$, —C(O)N(R$^3$)$_2$, —N(R$^3$)$_2$, —SO$_2$—R$^3$, —SO$_2$—N(R$^3$)$_2$, —N—C(O)—N(R$^3$)$_2$, —N—SO$_2$—N(R$^3$)$_2$, halogen, —C(halogen)$_b$R$^3_{(3-b)}$, —CN, —NR$^4$R$^5$—, —C(O)NR$^4$R$^5$, where R$^4$ and R$^5$ together with the nitrogen to which they are attached form a 5- to 7-membered heterocycle;
b is from 1 to 3;
a is 1 or 2; and
each R$^3$ is independently H, C$_1$-C$_{10}$ alkyl, aryl or heteroaryl.

It has been surprisingly found that these compounds are inhibitors of PI3K-p110δ. Some of the compounds disclosed herein may additionally inhibit PI3K-p 110β.

DESCRIPTION OF THE PREFERRED EMBODIMENTS

As used herein, alkyl means a C$_1$-C$_{10}$ alkyl group, which can be linear or branched. Preferably, it is a C$_1$-C$_6$ alkyl moiety. More preferably, it is a C$_1$-C$_4$ alkyl moiety. Examples include methyl, ethyl, n-propyl and t-butyl. It may be divalent, e.g. propylene.

As used herein, cycloalkyl contains from 3 to 10 carbon atoms. It may be monovalent or divalent.

As used herein, alkenyl means a C$_2$-C$_{10}$ alkenyl group. Preferably, it is a C$_2$-C$_6$ alkenyl group. More preferably, it is a C$_2$-C$_4$ alkenyl group. The alkenyl radicals may be mono- or di-saturated, more preferably monosaturated. Examples include vinyl, allyl, 1-propenyl, isopropenyl and 1-butenyl. It may be divalent, e.g. propenylene As used herein, alkynyl is a C$_2$-C$_{10}$ alkynyl group which can be linear or branched. Preferably, it is a C$_2$-C$_4$ alkynyl group or moiety. It may be divalent.

Each of the C$_1$-C$_{10}$ alkyl, C$_2$-C$_{10}$ alkenyl and C$_2$-C$_{10}$ alkynyl groups may be optionally substituted with each other, i.e. C$_1$-C$_{10}$ alkyl optionally substituted with C$_2$-C$_{10}$ alkenyl. They may also be optionally substituted with aryl, cycloalkyl (preferably C$_3$-C$_{10}$), aryl or heteroaryl.

As used herein, aryl means a monocyclic, bicyclic, or tricyclic monovalent or divalent aromatic radical, such as phenyl, biphenyl, naphthyl, anthracenyl, which can be optionally substituted with up to five substituents preferably selected from the group of C$_1$-C$_6$ alkyl, hydroxy, C$_1$-C$_3$ hydroxyalkyl, C$_1$-C$_3$ alkoxy, C$_1$-C$_3$ haloalkoxy, amino. C$_1$-C$_3$ mono alkylamino. C$_1$-C$_3$ bis alkylamino. C$_1$-C$_3$ acylamino, C$_1$-C$_3$ aminoalkyl, mono (C$_1$-C$_3$ alkyl) amino C$_1$-C$_3$ alkyl, bis(C$_1$-C$_3$ alkyl) amino C$_1$-C$_3$ alkyl, C$_1$-C$_3$-acylamino. C$_1$-C$_3$ alkyl sulfonylamino, halo, nitro, cyano, trifluoromethyl, carboxy, C$_1$-C$_3$ alkoxycarbonyl, aminocarbonyl, mono C$_1$-C$_3$ alkyl aminocarbonyl, bis C$_1$-C$_3$ alkyl aminocarbonyl, —SO$_3$H, C$_1$-C$_3$ alkylsulfonyl, aminosulfonyl, mono C$_1$-C$_3$ alkyl aminosulfonyl and bis C$_1$-C$_3$-alkyl aminosulfonyl.

As used herein, heteroaryl means a monocyclic, bicyclic or tricyclic monovalent aromatic radical containing up to four heteroatoms selected from oxygen, nitrogen and sulfur, such as thiazolyl, tetrazolyl, imidazolyl, oxazolyl, isoxazolyl, thienyl, pyrazolyl, pyridinyl, pyrazinyl, pyrimidinyl, indolyl, quinolyl, isoquinolyl, said radical being optionally substituted with up to three substituents preferably selected from the group of C$_1$-C$_6$ alkyl, hydroxy, C$_1$-C$_3$ hydroxyalkyl, C$_1$-C$_3$ alkoxy, C$_1$-C$_3$ haloalkoxy, amino, C$_1$-C$_3$ mono alkylamino, C$_1$-C$_3$ bis alkylamino, C$_1$-C$_3$ acylamino, C$_1$-C$_3$ aminoalkyl, mono (C$_1$-C$_3$ alkyl) amino C$_1$-C$_3$ alkyl, bis (C$_1$-C$_3$ alkyl) amino C$_1$-C$_3$ alkyl, C$_1$-C$_3$-acylamino, C$_1$-C$_3$ alkyl sulfonylamino, halo, nitro, cyano, trifluoromethyl, carboxy, C$_1$-C$_3$ alkoxycarbonyl, aminocarbonyl, mono C$_1$-C$_3$ alkyl aminocarbonyl, bis C$_1$-C$_3$ alkyl aminocarbonyl, -SO$_3$H, C$_1$-C$_3$ alkylsulphonyl, aminosulfonyl, mono C$_1$-C$_3$ alkyl aminosulfonyl and bis C$_1$-C$_3$-alkyl aminosulfonyl.

As used herein, heterocycle is a mono- or di-valent carbocyclic radical containing up to 4 heteroatoms selected from oxygen, nitrogen and sulphur. The word 'linker' has been used herein to mean di-valent. If the heterocycle is a di-valent linker, the heterocycle may be attached to neighbouring groups through a carbon atom, or through on of the heteroatoms, e.g. a N.

The heterocyclic ring may be mono- or di-saturated. The radical may be optionally substituted with up to three substituents independently selected from C$_1$-C$_6$ alkyl, hydroxy, C$_1$-C$_3$ hydroxyalkyl, C$_1$-C$_3$ alkoxy, C$_1$-C$_3$ haloalkoxy, amino, C$_1$-C$_3$ mono alkylamino, C$_1$-C$_3$ bis alkylamino, C$_1$-C$_3$ acylamino, C$_1$-C$_3$ aminoalkyl, mono (C$_1$-C$_3$ alkyl) amino C$_1$-C$_3$ alkyl, bis (C$_1$-C$_3$ alkyl) amino C$_1$-C$_3$ alkyl, C$_1$-C$_3$-acylamino, C$_1$-C$_3$ alkyl sulfonylamino, halo e.g. F, nitro, cyano, trifluoromethyl, carboxy, C$_1$-C$_3$ alkoxycarbonyl, aminocarbonyl, mono C$_1$-C$_3$ alkyl aminocarbonyl, bis C$_1$-C$_3$ alkyl aminocarbonyl, —SO$_3$H, C$_1$-C$_3$ alkylsulphonyl, aminosulfonyl, mono C$_1$-C$_3$ alkyl aminosulfonyl and bis C$_1$-C$_3$-alkyl aminosulfonyl.

As used herein, the above groups can be followed by the suffix -ene. This means that the group is divalent, i.e. a linker group.

In a preferred embodiment R$^1$ is represented by any of the following structures:

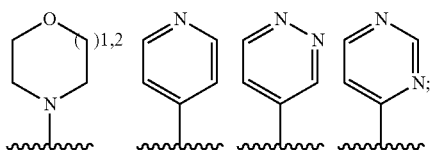

Preferably, W is S. More preferably, W is O.

R$^2$ may be attached to any suitable atom on the aryl group, as depicted in general formula I. Preferably, it is attached to atoms 2 or 3, as shown below:

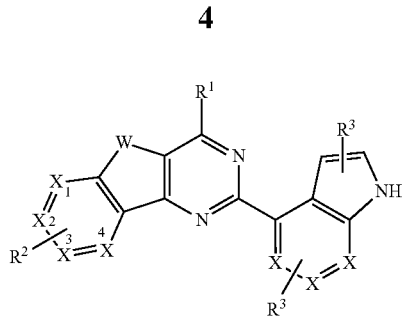

It may also be attached to atoms 1 or 4.

Preferably, a compound of the invention is of the structure:

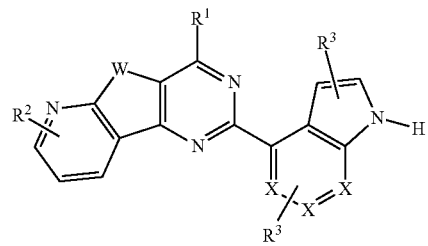

As above, the placing of any of the R$^2$ and R$^3$ groups has no significance, other than the group must be attached to that particular aryl system. In other words, the R2 group has 4 possible bonding positions, the first R$^3$ group has only 2 possible positions of attachment, and the other R$^3$ group may be attached to one of 3 positions.

More preferably, a compound of the invention has the formula:

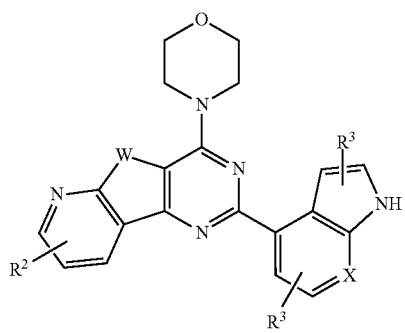

Preferably the 6,5-ring system in formula I is an indole. Alternatively, it may be a benzo-fused pyrrolo, a pyridyl-fused pyrrolo, a pyridazinyl-fused pyrrolo, a pyrazinyl-fused pyrrolo, or a pyrimidinyl-fused pyrrolo.

Preferably, both of the R$^3$ groups that are attached to the 6,5 ring system in formula I are H.

Preferably, at least one Q is —C(O)—NR$^4$R$^5$, where R$^4$ and R$^5$ together with the nitrogen to which they are attached form a 5 to 7-membered heterocycle linker. More preferably, Q is

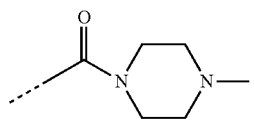

Preferably, at least one Q is —NR³—

Preferably, at least one Q is a direct bond.

Preferably, at least one L is $C_1$-$C_{10}$ alkylene or at least one L is $C_2$-$C_{10}$ alkenylene, or at least one L is cyloalkylene.

Preferably Y is $N(R^3)_2$. More preferably, Y is a heteroaryl, such as an indolyl, or Y is a heterocycle.

Preferably $R^2$ is H. Preferably $R^2$ is —($C_1$-$C_{10}$ alkylene)-$N(R^3)_2$. More preferably, $R^2$ is —$CH_2$—$N(CH_3)_2$. $R^2$ may also be —($C_2$-$C_{10}$ alkenylene)-C(O)—N($R^4R^5$)—$R^3$, where $R_4$ and $R_5$ together with the nitrogen to which they are attached form a 5- to 7-membered heterocycle. More preferably, $R^2$ is

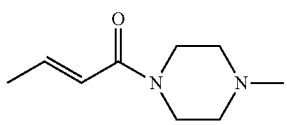

Still more preferably, $R^2$ comprises —($C_1$-$C_{10}$ alkylene)-$NR^4R^5$ or $R^2$ comprises —($C_1$-$C_{10}$ alkylene)-$NR^3$—($C_1$-$C_{10}$ alkylene)-cycloakyl, wherein $R^2$, $R^4$ and $R^5$ are as defined above.

Preferably m is 0, 1 or 2.

Examples of structures embodying the invention are:

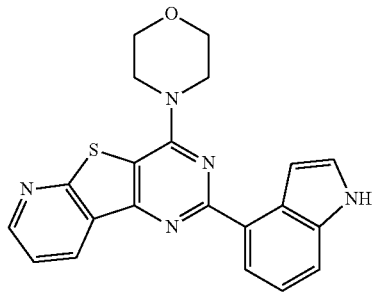

A

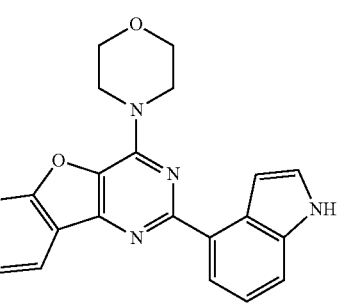

B

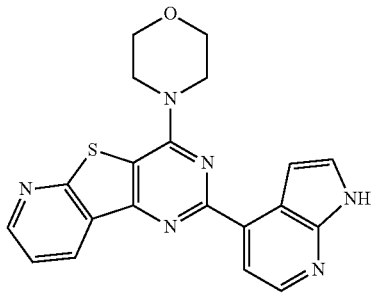

C

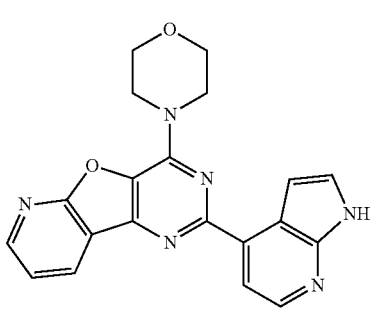

D

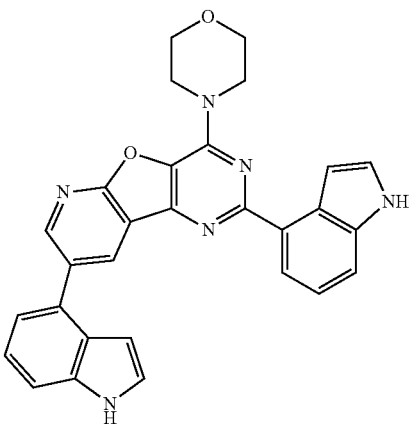

E

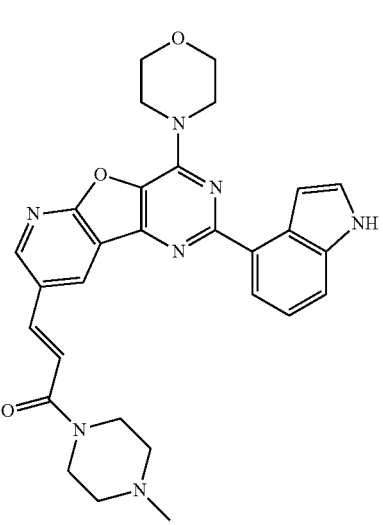

F

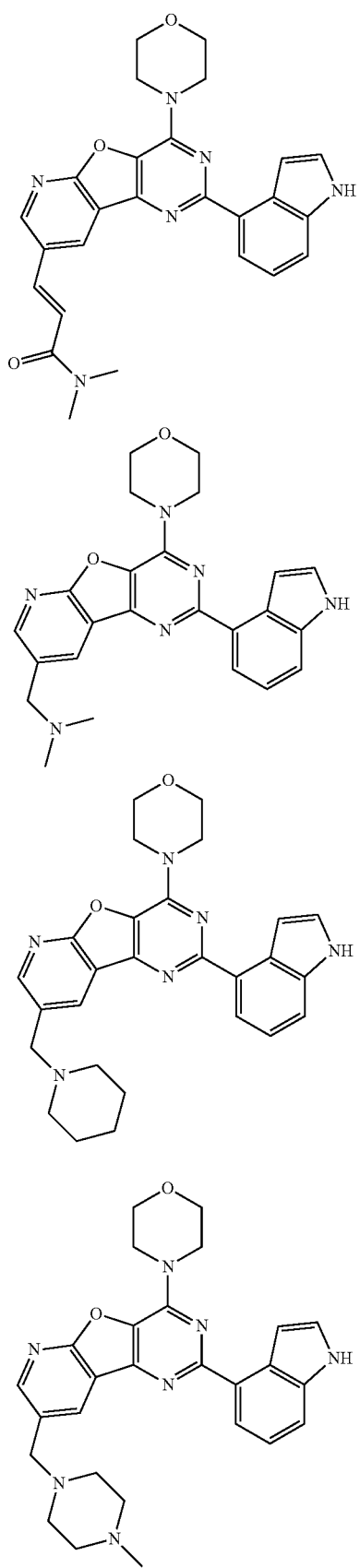
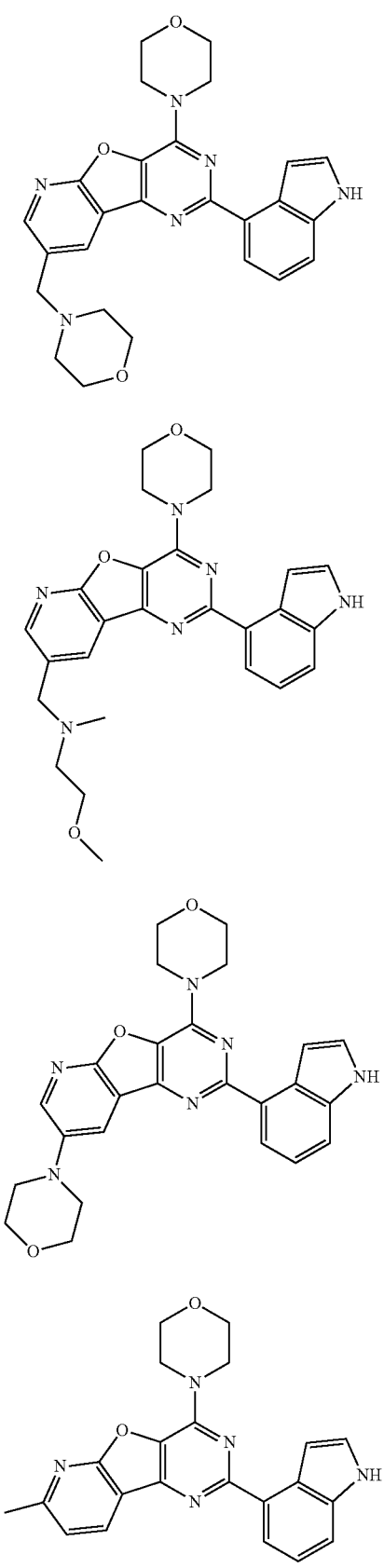

-continued

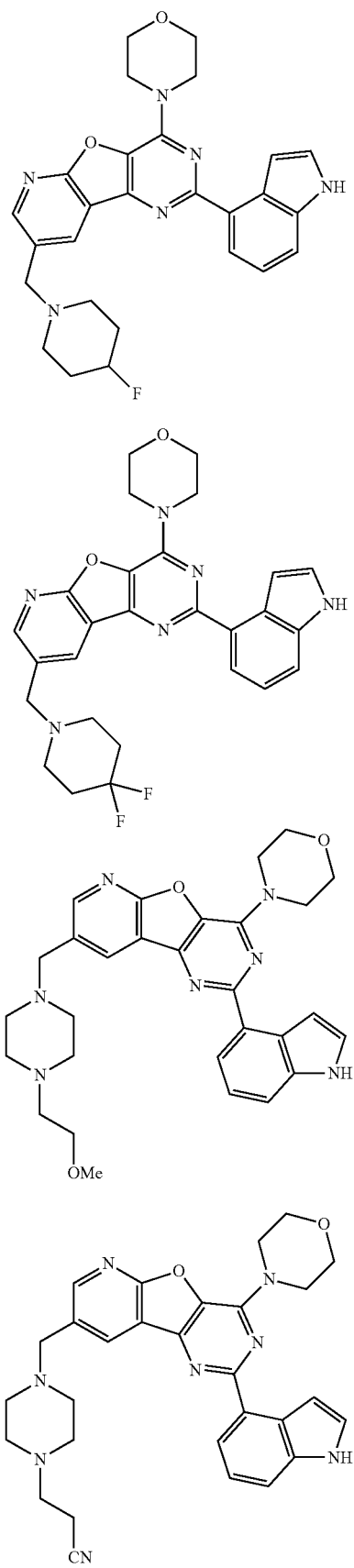

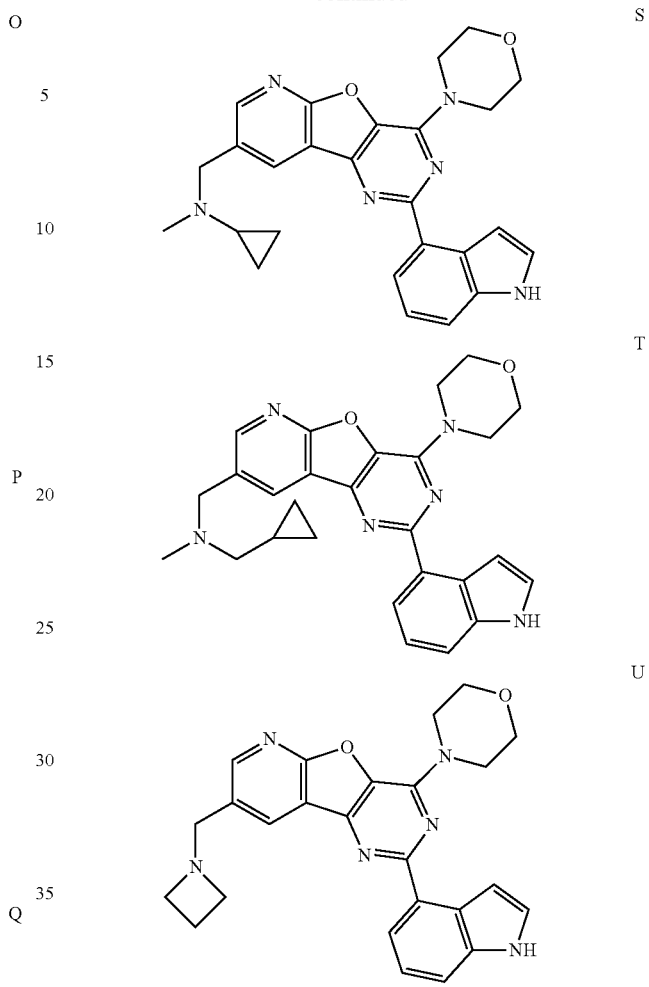

A pharmaceutical composition of the invention typically contains up to 85 wt % of a compound of the invention. More typically, it contains up to 50 wt % of a compound of the invention. Preferred pharmaceutical compositions are sterile and pyrogen-free. Further, the pharmaceutical compositions provided by the invention typically contain a compound of the invention which is a substantially pure optical isomer. Preferably, the pharmaceutical composition comprises a pharmaceutically acceptable salt form of a compound of the invention.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, salicylic, stearic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aryl amines or heterocyclic amines.

For the avoidance of doubt, the present invention also embraces prodrugs which react in vivo to give a compound of the present invention.

The compounds of the invention may be prepared by synthetic routes that will be apparent to those skilled in the art, e.g. based on the Examples.

The compounds of the invention and compositions comprising them may be administered in a variety of dosage forms. In one embodiment, a pharmaceutical composition comprising a compound of the invention may be formulated in a format suitable for oral, rectal, parenteral, intranasal or transdermal administration or administration by inhalation or by suppository. Typical routes of administration are parenteral, intranasal or transdermal administration or administration by inhalation.

The compounds of the invention can be administered orally, for example as tablets, troches, lozenges, aqueous or oily suspensions, dispersible powders or granules. Preferred pharmaceutical compositions of the invention are compositions suitable for oral administration, for example tablets and capsules.

The compounds of the invention may also be administered parenterally, whether subcutaneously, intravenously, intramuscularly, intrasternally, transdermally or by infusion techniques. The compounds may also be administered as suppositories.

The compounds of the invention may also be administered by inhalation. An advantage of inhaled medications is their direct delivery to the area of rich blood supply in comparison to many medications taken by oral route. Thus, the absorption is very rapid as the alveoli have an enormous surface area and rich blood supply and first pass metabolism is bypassed. A further advantage may be to treat diseases of the pulmonary system, such that delivering drugs by inhalation delivers them to the proximity of the cells which are required to be treated.

The present invention also provides an inhalation device containing such a pharmaceutical composition. Typically said device is a metered dose inhaler (MDI), which contains a pharmaceutically acceptable chemical propellant to push the medication out of the inhaler.

The compounds of the invention may also be administered by intranasal administration. The nasal cavity's highly permeable tissue is very receptive to medication and absorbs it quickly and efficiently, more so than drugs in tablet form. Nasal drug delivery is less painful and invasive than injections, generating less anxiety among patients. By this method absorption is very rapid and first pass metabolism is usually bypassed, thus reducing inter-patient variability. Further, the present invention also provides an intranasal device containing such a pharmaceutical composition.

The compounds of the invention may also be administered by transdermal administration. The present invention therefore also provides a transdermal patch containing a compound of the invention.

The compounds of the invention may also be administered by sublingual administration. The present invention therefore also provides a sub-lingual tablet comprising a compound of the invention.

A compound of the invention may also be formulated with an agent which reduces degradation of the substance by processes other than the normal metabolism of the patient, such as anti-bacterial agents, or inhibitors of protease enzymes which might be the present in the patient or in commensural or parasite organisms living on or within the patient, and which are capable of degrading the compound.

Liquid dispersions for oral administration may be syrups, emulsions and suspensions.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

The compounds of the present invention can be used in both the treatment and prevention of cancer and can be used in a monotherapy or in a combination therapy. When used in a combination therapy, the compounds of the present invention are typically used together with small chemical compounds such as platinum complexes, anti-metabolites. DNA topoisomerase inhibitors, radiation, antibody-based therapies (for example herceptin and rituximab), anti-cancer vaccination, gene therapy, cellular therapies, hormone therapies or cytokine therapy.

In one embodiment of the invention a compound of the invention is used in combination with another chemotherapeutic or antineoplastic agent in the treatment of a cancer. Examples of such other chemotherapeutic or antineoplastic agents include platinum complexes including cisplatin and carboplatin, mitoxantrone, vinca alkaloids for example vincristine and vinblastine, anthracycline antibiotics for example daunorubicin and doxorubicin, alkylating agents for example chlorambucil and melphalan, taxanes for example paclitaxel, antifolates for example methotrexate and tomudex, epipodophyllotoxins for example etoposide, camptothecins for example irinotecan and its active metabolite SN38 and DNA methylation inhibitors for example the DNA methylation inhibitors disclosed in WO02/085400.

According to the invention, therefore, products are provided which contain a compound of the invention and another chemotherapeutic or antineoplastic agent as a combined preparation for simultaneous, separate or sequential use in alleviating a cancer. Also provided according to the invention is the use of compound of the invention in the manufacture of a medicament for use in the alleviation of cancer by coadministration with another chemotherapeutic or antineoplastic agent. The compound of the invention and the said other agent may be administrated in any order. In both these cases the compound of the invention and the other agent may be administered together or, if separately, in any order as determined by a physician.

The PI3K inhibitors of the present invention may also be used to treat abnormal cell proliferation due to insults to body tissue during surgery. These insults may arise as a result of a variety of surgical procedures such as joint surgery, bowel surgery, and cheloid scarring. Diseases that produce fibrotic tissue that may be treated using the PI3K inhibitors of the present invention include emphysema. Repetitive motion disorders that may be treated using the present invention include carpal tunnel syndrome. An example of a cell proliferative disorder that may be treated using the invention is a bone tumour.

Proliferative responses associated with organ transplantation that may be treated using PI3K inhibitors of the invention include proliferative responses contributing to potential organ rejections or associated complications. Specifically, these proliferative responses may occur during transplantation of the heart, lung, liver, kidney, and other body organs or organ systems.

Abnormal angiogenesis that may be treated using this invention include those abnormal angiogenesis accompanying rheumatoid arthritis, ischemic-reperfusion related brain edema and injury, cortical ischemia, ovarian hyperplasia and hypervascularity, polycystic ovary syndrome, endometriosis, psoriasis, diabetic retinopathy, and other ocular angiogenic diseases such as retinopathy of prematurity (retrolental fibroplastic), macular degeneration, corneal graft rejection, neuroscular glaucoma and Oster Webber syndrome.

Examples of diseases associated with uncontrolled angiogenesis that may be treated according to the present invention include, but are not limited to retinal/choroidal neovascularisation and corneal neovascularisation. Examples of diseases which include some component of retinal/choroidal neovascularisation include, but are not limited to. Best's diseases, myopia, optic pits. Stargart's diseases, Paget's disease, vein occlusion, artery occlusion, sickle cell anaemia, sarcoid, syphilis, pseudoxanthoma elasticum carotid apo structive diseases, chronic uveitis/vitritis, mycobacterial infections. Lyme's disease, systemic lupus erythematosus, retinopathy of prematurity. Eale's disease, diabetic retinopathy, macular degeneration. Bechet's diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularisation of the angle) and diseases caused by the abnormal proliferation of fibrovascular or fibrous tissue including all forms of proliferative vitreoretinopathy. Examples of corneal neovascularisation include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection. Mooren ulcer, Terrien's marginal degeneration, marginal keratolysis, polyarteritis. Wegener sarcoidosis, Scleritis, periphigoid radial keratotomy, neovascular glaucoma and retrolental fibroplasia, syphilis. Mycobacteria infections, lipid degeneration, chemical burns, bacterial ulcers, fungal ulcers. Herpes simplex infections. Herpes zoster infections, protozoan infections and Kaposi sarcoma.

Chronic inflammatory diseases associated with uncontrolled angiogenesis may also be treated using PI3K inhibitors of the present invention. Chronic inflammation depends on continuous formation of capillary sprouts to maintain an influx of inflammatory cells. The influx and presence of the inflammatory cells produce granulomas and thus maintains the chronic inflammatory state. Inhibition of angiogenesis using a PI3K inhibitor alone or in conjunction with other anti-inflammatory agents may prevent the formation of the granulosmas and thus alleviate the disease. Examples of chronic inflammatory diseases include, but are not limited to, inflammatory bowel diseases such as Crohn's disease and ulcerative colitis, psoriasis, sarcoidosis, and rheumatoid arthritis.

Inflammatory bowel diseases such as Crohn's disease and ulcerative colitis are characterised by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhoea associated with abdominal pain, fever, anorexia, weight loss and abdominal swelling. Ulcerative colitis is also a chronic, nonspecific, inflammatory and ulcerative disease arising in the colonic mucosa and is characterised by the presence of bloody diarrhoea. These inflammatory bowel diseases are generally caused by chronic granulomatous inflammation throughout the gastrointestinal tract, involving new capillary sprouts surrounded by a cylinder of inflammatory cells. Inhibition of angiogenesis by these inhibitors should inhibit the formation of the sprouts and prevent the formation of granulomas. Inflammatory bowel diseases also exhibit extra intestinal manifestations, such as skin lesions. Such lesions are characterized by inflammation and angiogenesis and can occur at many sites other the gastrointestinal tract. Inhibition of angiogenesis by PI3K inhibitors according to the present invention can reduce the influx of inflammatory cells and prevent lesion formation.

Sarcoidosis, another chronic inflammatory disease, is characterized as a multisystem granulomatous disorder. The granulomas of this disease can form anywhere in the body. Thus, the symptoms depend on the site of the granulomas and whether the disease is active. The granulomas are created by the angiogenic capillary sprouts providing a constant supply of inflammatory cells. By using PI3K inhibitors according to the present invention to inhibit angiogenesis, such granulomas formation can be inhibited. Psoriasis, also a chronic and recurrent inflammatory disease, is characterised by papules and plaques of various sizes. Treatment using these inhibitors alone or in conjunction with other anti-inflammatory agents should prevent the formation of new blood vessels necessary to maintain the characteristic lesions and provide the patient relief from the symptoms.

Rheumatoid arthritis (RA) is also a chronic inflammatory disease characterised by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using PI3K inhibitors according to the present invention alone or in conjunction with other anti-RA agents may prevent the formation of new blood vessels necessary to maintain the chronic inflammation.

Preferably, the condition is cancer, notably leukaemias including chronic myelogenous leukaemia and acute myeloid leukaemia, lymphomas, solid tumours, and PTEN-negative tumours including PTEN-negative haematological, breast, lung, endometrial, skin, brain and prostrate cancers (where PTEN refers to "phosphatise and tensin homolog deleted on chromosome 10"). More preferably, the condition to be treated by a compound of the invention is rheumatoid arthritis, asthma, chronic obstructive pulmonary disease (COPD), multiple sclerosis, psoriasis and other inflammatory skin disorders, systemic lupus erythematosus, inflammatory bowel disease, and organ transplant rejection. More preferably, The invention will now be illustrated by the following Examples.

EXAMPLES

Example A 2-(1H-Indol-4-yl)-4-morpholin-4-yl-pyrido[3',2':4,5]thieno[3,2-d]pyrimidine

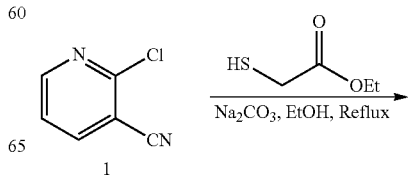

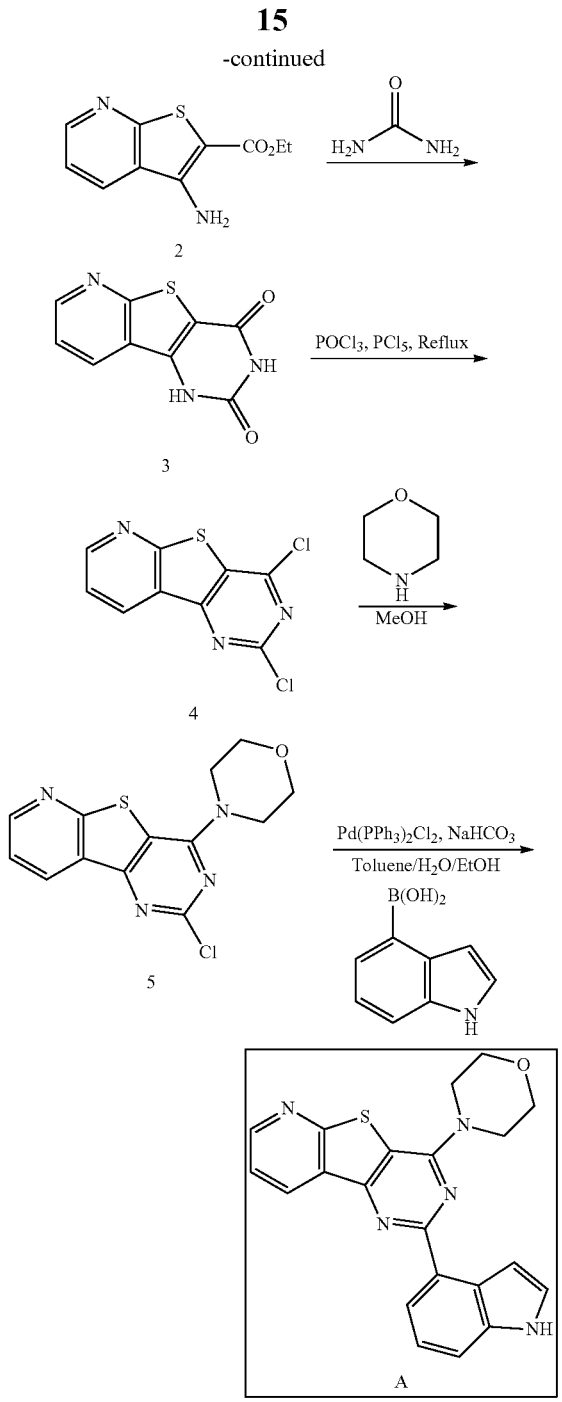

i. 3-Amino-thieno[2,3-b]pyridine-2-carboxylic acid ethyl ester, 2

Under Ar(g), 2-chloro-3-pyridinecarbonitrile, 1. (3.026 g, 21.8 mmol) and sodium carbonate (2.511 g, 23.7 mmol) were dissolved in dry ethanol (11.5 mL). Ethyl-2-meracaptacetate (3.1 mL, 28.3 mmol) was then added, and the reaction mixture was heated at reflux for 4 h 35 min. The reaction was then cooled to rt; water (140 mL) was then added, at which point a precipitate formed, and the resulting reaction mixture was subsequently stirred for a further 30 min. The precipitate was filtered, washed with water (2×15 mL) and the resulting residue collected and dried under vacuum to furnish 2 (4.435 g, 20 mmol, 92%) as an orange solid.

$^1$H NMR (400 MHz, CDCl$_3$) δ$_H$: 8.70 (dd, J=4.6, 1.44 Hz, 1H), 7.96 (dd, J=8.1, 1.57Hz, 1H), 7.33 (dd, J=8.2, 4.6Hz, 1H), 5.92 (br. s, 2H), 4.38 (q, J=7.1Hz, 2H), 1.41 (t, J=7.2 Hz, 3H).

MS (ES$^+$) 223.0 (100%, [M+H]$^+$).

ii. 1H-Pyrido[3',2':4,5]thieno[3,2-d]pyrimidine-2,4-dione, 3

Under Ar(g), compound 2 (518 mg, 2.33 mmol) and urea (1.143 g, 19.0 mmol) were combined and heated to 190° C. with stirring for 2.5 h. The reaction mixture was then cooled, and 1M NaOH (10 mL) was added while the mixture was warm; the resulting mixture was then stirred and filtered. The filtrate was acidified with 1M HCl, and a precipitate formed; the mixture was then filtered and the solid collected dried under vacuum to furnish 3 as an orange/brown solid (125 mg, 0.574 mmol, 25%).

$^1$H NMR (400MHz, DMSO-d$_6$) δ$_H$: 12.40 (s, 1H), 11.60 (s, 1H), 8.80-8.73 (m, 2H), 7.63 (dd, J=8.2, 4.6 Hz, 1H).

MS (ES$^-$) 217.9 (100%, [M−H]$^-$).

iii. 2,4-Dichloro-pyrido[3',2':4,5]thieno[3,2-d]pyrimidine, 4

To compound 3 (15.2 mg, 0.070 mmol) and PCl$_5$ (592.2 mg, 2.84 mmol) under Ar(g) was added POCl$_3$ (2 mL), and the resulting reaction mixture was then heated at reflux for 26 h. The POCl$_3$ was then removed in vacuo to yield a solid residue which was slowly added to crushed ice (4 g) with stirring. The aqueous phase was then extracted with CHCl$_3$, the layers were separated and the organic phase was washed with water to remove all the remaining phosphoric acid. The organic layer was subsequently dried (MgSO$_4$) and concentrated in vacuo to give 4 (3.8 mg, 0.015 mmol, 21%).

$^1$H NMR (300MHz, CDCl$_3$) δ$_H$: 8.93 (dd, J=4.7, 1.7Hz, 1H), 8.78 (dd, J=7.9, 1.5Hz, 1H), 7.61 (m, 1H).

MS (ES$^+$) 255.9 (100%, [M+H]$^+$).

iv. 2-Chloro-4-morpholin-4-yl-pyrido[3',2':4,5]thieno[3,2-d]pyrimidine, 5

To 4 (34.3 mg, 0.14 mmol) in methanol (1.5 mL) was added morpholine (25 μL, 0.29 mmol) dropwise, and the resulting reaction was stirred for 1 h at rt. The mixture was then filtered, washed with water and then methanol, and the remaining solid was dissolved in CH$_2$Cl$_2$ and concentrated in vacuo to furnish 5 as a pale brown solid (30.1 mg, 0.098 mmol, 73%).

$^1$H NMR (300MHz, CDCl$_3$) δ$_H$: 8.83 (br. s, 1H), 8.72 (dd, J=8.0, 1.51Hz, 1H), 7.53 (m, 1H), 4.11-4.05 (m, 4H), 3.94-3.88 (m, 4H).

MS (ES$^+$) 307.0 (100%, [M+H]$^+$).

v. 2-(1H-Indol-4-yl)-4-morpholin-4-yl-pyrido[3',2':4,5]thieno[3,2-d]pyrimidine, A Under Ar(g), to a mixture of compound 5 (14.97 mg, 0.049 mmol), indole-4-boronic acid (8.70 mg, 0.054 mmol), dichloro-bis(triphenylphosphine)palladium (II) (1.81 mg, 0.0026 mmol) and sodium hydrogen carbonate (12.50 mg, 0.15 mmol) was added ethanol (0.75 mL) followed by toluene (1.25 mL) and then water (0.35 mL). The reaction was then heated in a microwave at 120° C. (300 W) for 1 h. The reaction nl/xtuvevvas then cooled to rt, and was partitioned between CH$_2$Cl$_2$ and water, and the organic layer was then separated, dried (MgSO$_4$) and concentrated in vacuo. Purification by flash column chromatography on silica (eluant 0:1-1:99) MeOH/CH$_2$Cl$_2$) furnished A (1 mg, 0.0026 mol, 5%) as a white solid.

$^1$H NMR (300 MHz, CDCl$_3$) δ$_H$: 8.91 (d, J=8.3Hz, 1H) 8.82 (dd, J=4.7, 1.7Hz, 1H) 8.40-8.33 (m, 2H), 7.72 (br. s, 1H), 7.54 (d, J=1.1Hz, 1H), 7.54 (dd, J=12.8, 4.9Hz, 1H), 7.42-7.32 (m, 2H), 4.19-4.11 (m, 4H), 4.01-3.93 (m, 4H).

MS (ES$^+$) 388.1 (100%, [M+H]$^+$).

Example B 2-(1H-Indol-4-yl)-4-morpholin-4-yl-pyrido[3',2':4,5]furo[3,2-d]pyrimidine

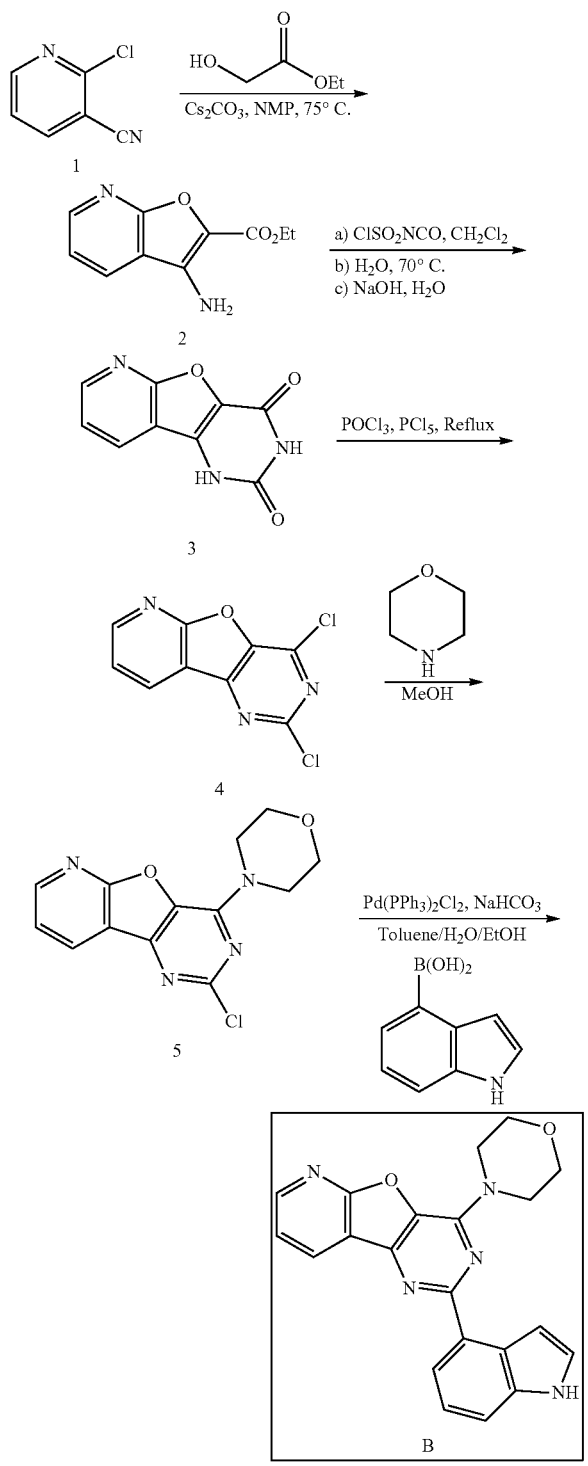

i. 3-Amino-furo[2,3-b]pyridine-2-carboxylic acid ethyl ester, 2

2-Chloro-3-pyridinecarbonitrile, 1, (4.00 g, 28.9 mmol), $Cs_2CO_3$ (28.2 g, 86.6 mmol) and ethyl glycolate (3 mL, 31.7 mmol) were placed in a flask under Ar(g). Dry NMP was added, and the suspension was heated at 75° C. for 20 h with vigorous stirring. The reaction mixture was cooled to rt, whereupon water (200 mL) and $Et_2O$ (3×100 mL) were added. The organic layers were combined, washed with water (3×15 mL) before being dried ($MgSO_4$) and concentrated in vacuo. Purification by flash column chromatography on silica (eluant 15-40% EtOAc/Hex) gave 2 (2.41 g, 11.7 mmol, 40%) as a white solid.

$^1$H NMR (400 MHz, $CDCl_3$) $\delta_H$: 8.51 (dd, J=5.0, 2.0Hz, 1H), 7.96 (dd, J=8.0, 2.0Hz, 1H), 7.23-7.28 (m, 1H), 4.44 (q, J=7.0 Hz, 2H), 4.01 (br. s., 2H), 1.44 (t, J=7.0 Hz, 3H).

MS (ES$^+$) 229 (100%, [M+Na]$^+$).

ii. 1H-Pyrido[3',2':4,5]furo[3,2-d]pyrimidine-2,4-dione, 3

Under Ar(g), and at 0° C., to a solution of compound 2 (1.189 g, 5.77 mmol) in $CH_2Cl_2$ (20 mL) was added dropwise chlorosulfonyl isocyanate (0.55 mL, 6.34 mmol). The reaction mixture was allowed to warm to rt and after 4 h it was concentrated in vacuo. Water (20 mL) was added, and the suspension was stirred vigorously while heating to 70° C. for 10 min [MS analysis showed formation of the urea intermediate was complete]. The mixture was then cooled and filtered, washing with water. The resulting solid cake (0.87 g) was subsequently suspended in water (61 mL) and NaOH (3.15 g) was added. After 1 h stirring, LCMS analysis confirmed that the reaction had gone to completion. The mixture was then filtered, washing with water, to furnish 3 (460 mg, 2.3 mmol, 40%) as a white solid.

$^1$H NMR (400 MHz, DMSO-$d_6$) $\delta_H$: 12.06 (br. s., 1H), 11.49 (br. s., 1H), 8.60 (dd, J=5.0, 1.5Hz, 1H), 8.43 (dd, J=8.0, 2.0Hz, 1H), 7.56 (dd, J=8.0, 5.0Hz, 1H).

MS (ES$^-$) 202 (100%, [M–H]$^-$).

iii. 2,4-Dichloro-pyrido[3',2':4,5]furo[3,2-d]pyrimidine, 4

To compound 3 (0.14 g, 0.70 mmol) and $PCl_5$ (2.4 g, 2.84 mmol) under Ar(g) was added $POCl_3$ (8 mL), and the resulting reaction mixture was then heated at reflux for 20 h. After the mixture had been cooled to rt it was poured onto crushed ice (200 mL) with vigorous stirring. The aqueous phase was then extracted with $CH_2Cl_2$ (3×50 mL). The combined organic layers were subsequently dried ($MgSO_4$) and concentrated in vacuo to give 4 (66 mg, 0.28 mmol, 40%) as an off-white solid.

$^1$H NMR (400 MHz, $CDCl_3$) $\delta_H$: 8.80 (dd, J=5.0, 1.5Hz, 1H), 8.64 (dd, J=8.0, 2.0Hz, 1H), 7.61 (dd, J=7.5, 5.0Hz, 1H).

iv. 2-Chloro-4-morpholin-4-yl-pyrido[3',2':4,5]furo[3,2-d]pyrimidine, 5

To a solution of 4 (64 mg, 0.27 mmol) in dry methanol (10 mL) was added morpholine (55 μL, 0.62 mmol) dropwise, and the resulting reaction was stirred for 2 h at rt. The resulting precipitate was then filtered, washed with water and then a mixture of 5:1 methanol/water, and the remaining solid was dried in vacuo to furnish 5 (50 mg, 0.17 mmol, 64%) as a white solid.

$^1$H NMR (400MHz, $CDCl_3$) $\delta_H$: 8.63 (dd, J=5.0, 2.0Hz, 1H), 8.52 (dd, J=7.5, 2.0Hz, 1H), 7.48 (dd, J=7.5, 5.0Hz, 1H), 4.10-4.23 (m, 4H), 3.86-3.91 (m, 4H).

MS (ES$^+$) 291 (100%, [M–H]$^+$).

v. 2-(1H-Indol-4-yl)-4-morpholin-4-yl-pyrido[3',2':4,5]furo[3,2-d]pyrimidine, B

Under Ar(g), to a mixture of compound 5 (25 mg, 0.086 mmol), indole-4-boronic acid (15.2 mg, 0.095 mmol), dichloro-bis(triphenylphosphine)palladium (II) (3 mg, 0.004 mmol) and sodium hydrogen carbonate (22 mg, 0.26 mmol) was added ethanol (1 mL) followed by toluene (1.6 mL) and then water (0.5 mL). The reaction mixture was then heated in a microwave at 120° C. (300 W) for 45 min, and was subsequently cooled to rt; the mixture was then partitioned between CH₂Cl₂ and water, and the organic layer was separated, dried (MgSO₄) and concentrated in vacuo. Purification by flash column chromatography on silica (eluant 30-60% EtOAc/Hex) furnished B (24.5 mg, 0.067 mol, 77%) as an off-white solid.

¹H NMR (400 MHz, 19:1 CDCl₃/CD₃OD) δ$_H$: 8.94 (br. s., 1H), 8.51 (dd, J=7.5, 2.0Hz, 1H), 8.40 (dd, J=5.0, 2.0Hz, 1H), 7.96 (d, J=7.5 Hz, 1H), 7.26-7.35 (m, 3H), 7.08-7.18 (m, 2H), 4.02-4.11 (m, 4H), 3.71-3.79 (m, 4H). ¹³C NMR (100 MHz, 19:1 CDCl₃/CD₃OD) δ$_C$: 162.6, 161.7, 149.4, 148.9, 147.0, 137.0, 133.0, 132.3, 130.3, 126.6, 125.2, 121.6, 121.5, 120.4, 115.5, 113.2, 103.7, 67.0, 45.9.

MS (ES⁺) 372 (100%, [M+H]⁺).

Example C

4-Morpholin-4-yl-2-(1H-pyrrolo[2,3-b]pyridin-4-yl)-pyrido[3',2':4,5]thieno[3,2d]pyrimidine

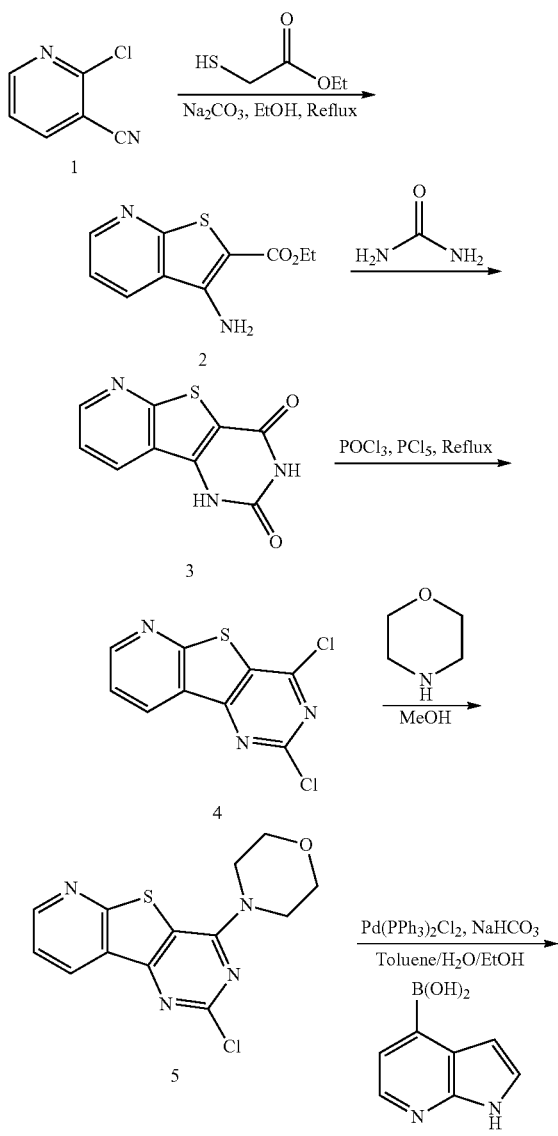

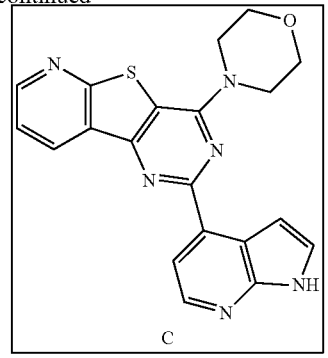

C i. 3-Amino-thieno[2,3-b]pyridine-2-carboxylic acid ethyl ester, 2

2-Chloro-3-pyridinecarbonitrile, 1, (3.026 g, 21.8 mmol) and sodium carbonate (2.511 g, 23.7 mmol) were dissolved in dry ethanol (11.5 mL) under Ar(g). Ethyl-2-meracaptacetate (3.1 mL, 28.3 mmol) was then added, and the reaction mixture was heated at reflux for 4.5 h. The reaction mixture was then cooled to rt; water (140 mL) was added, at which point a precipitate formed, and the resulting reaction mixture was subsequently stirred for a further 30 min. The precipitate was filtered, washed with water (2×15 mL) and the resulting residue collected and dried under vacuum to furnish 2 (4.435 g, 20 mmol, 92%) as an orange solid.

¹H NMR (400 MHz, CDCl₃) δ$_H$: 8.70 (dd, J=4.6, 1.44Hz, 1H), 7.96 (dd, J=8.1, 1.57Hz, 1H), 7.33 (dd, J=8.2, 4.6Hz, 1H), 5.92 (br. s, 2H), 4.38 (q, J=7.1Hz, 2H), 1.41 (t, J=7.2Hz, 3H).

MS (ES⁺) 223.0 (100%, [M+H]⁺).

ii. 1H-Pyrido[3',2':4,5]thieno[3,2-d]pyrimidine-2,4-dione, 3

Compound 2 (518 mg, 2.33 mmol) and urea (1.143 g, 19.0 mmol) were combined and heated to 190° C. with stirring for 2.5 h. The reaction mixture was then cooled, and 1M NaOH (10 mL) was added while the mixture was warm; the resulting mixture was then stirred and filtered. The aqueous layer was acidified with 1M HCl, and a precipitate formed; the mixture was then filtered and the solid collected dried under vacuum to furnish 3 as an orange/brown solid (125 mg, 0.574 mmol, 25%).

¹H NMR (400 MHz, DMSO-d₆) δ$_H$: 12.40 (s, 1H), 11.60 (s, 1H), 8.80-8.73 (m, 2H), 7.63 (dd, J=8.2, 4.6 Hz, 1H).

MS (ES⁻) 217.9 (100%, [M−H]⁻).

iii. 2,4-Dichloro-pyrido[3',2':4,5]thieno[3,2-d]pyrimidine, 4

To compound 3 (15.2 mg, 0.070 mmol) and PCl₅ (592 mg, 2.84 mmol) under Ar(g) was added POCl₃ (2 mL), and the resulting reaction mixture was then heated at reflux for 26 h. The POCl₃ was then removed in vacuo to furnish a solid residue, which was slowly added to crushed ice (50 g) with stirring. The aqueous phase was then extracted with CH₂Cl₂, the layers were separated and the organic phase was washed with water to remove all the remaining phosphoric acid. The organic layer was subsequently dried (MgSO₄) and concentrated in vacuo to give 4 (3.8 mg, 0.015 mmol, 21%).

¹H NMR (300 MHz, CDCl₃) δ$_H$: 8.93 (dd, J=4.7, 1.7 Hz, 1H), 8.78 (dd, J=7.9, 1.5 Hz, 1H), 7.61 (m, 1H).

MS (ES⁺) 255.9 (100%, [M+H]⁺).

iv. 2-Chloro-4-morpholin-4-yl-pyrido[3',2':4,5]thieno[3,2-d]pyrimidine, 5

To compound 4 (34.3 mg, 0.14 mmol) in dry methanol (1.5 mL) was added morpholine (25 µL, 0.29 mmol) in a dropwise fashion, and the resulting mixture was stirred for 1 h at rt. The mixture was then filtered, washed with water and then methanol, and the remaining solid was dissolved in CH₂Cl₂ and concentrated in vacuo to furnish 5 as a pale brown solid (30.1 mg, 0.098 mmol, 73%).

¹H NMR (300 MHz, CDCl₃) δ$_H$: 8.83 (br. s, 1H), 8.72 (dd, J=8.0, 1.51 Hz, 1H), 7.53 (m, 1H), 4.11-4.05 (m, 4H), 3.94-3.88 (m, 4H).

MS (ES⁺) 307.0 (100%, [M+H]⁺).

v. 4-Morpholin-4-yl-2-(1H-pyrrolo[2,3-b]pyridin-4-yl)-pyrido[3',2':4,5]thieno[3,2d]pyrimidine, C To a mixture of compound 5 (16.0 mg, 0.052 mmol), 7-azaindole-4-boronic acid pinacol ester (14.3 mg, 0.058 mmol), sodium hydrogen carbonate (13.5 mg, 0.16 mmol) and dichloro-bis(triphenylphosphine)palladium (II) (2.2 mg, 0.0031 mmol) was added toluene (1.25 mL) followed by ethanol (0.75 mL) and then distilled water (0.35 mL). The reaction mixture was then heated in a microwave at 120° C. (300 W) for 1 h, and was subsequently cooled to rt; the mixture was then partitioned between CH₂Cl₂ (40 mL) and water (40 mL), and the organic layer was separated, dried (MgSO₄) and concentrated in vacuo. Purification by flash column chromatography on silica (eluant 70-90% EtOAc/Hex) furnished C (4.81 mg, 0.012 mmol, 24%) as a pale green solid.

¹H NMR (400 MHz, 19:1 CDCl₃/CD₃OD) δ$_H$: 8.84 (dd, J=8.0, 1.5Hz, 1H), 8.81 (dd, J=4.8, 1.8Hz, 1H), 8.36 (d, J=5.5Hz, 1H), 8.25 (d, J=5.0Hz, 1H), 7.50-7.60 (m, 3H), 4.09-4.16 (m, 4H), 3.92-3.98 (m, 4H).

MS (ES⁺) 389 (100%, [M+H]⁺).

Example D

4-Morpholin-4-yl-2-(1H-pyrrolo[2,3-b]pyridin-4-yl)-pyrido[3',2':4,5]furo[3,2-d]pyrimidine

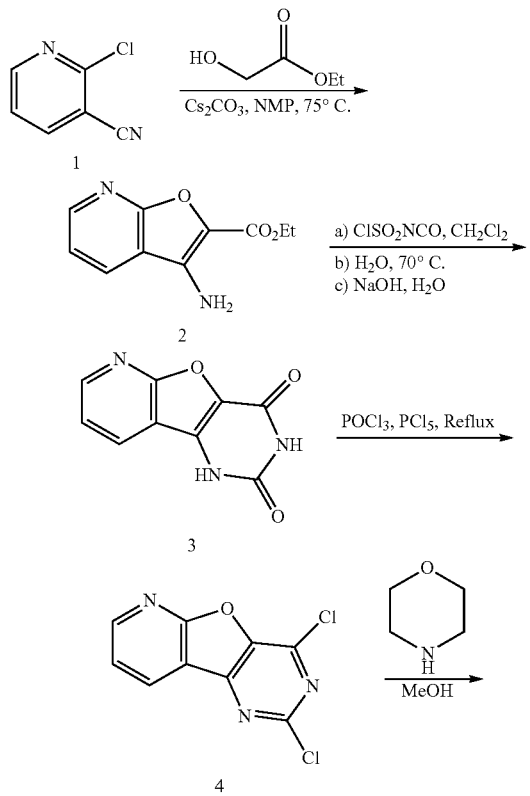

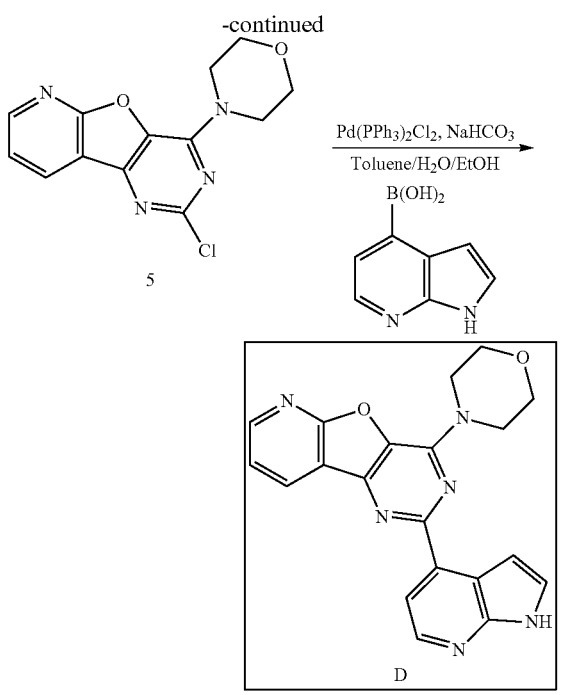

i. 3-Amino-furo[2,3-b]pyridine-2-carboxylic acid ethyl ester, 2

2-Chloro-3-pyridinecarbonitrile, 1, (4.00 g, 28.9 mmol), Cs₂CO₃ (28.2 g, 86.6 mmol) and ethyl glycolate (3 mL, 31.7 mmol) were placed in a flask under Ar(g). Dry NMP was added, and the suspension was heated at 75° C. for 20 h with vigorous stirring. The reaction mixture was cooled to rt whereupon water (200 mL) and Et₂O (3×100 mL) were added. The organic layers were combined, washed with water (3×15 mL) before being dried (MgSO₄) and concentrated in vacuo. Purification by flash column chromatography on silica (eluant 15-40% EtOAc/Hex) gave 2 (2.41 g, 11.7 mmol, 40%) as a white solid.

¹H NMR (400MHz, CDCl₃) δ$_H$: 8.51 (dd, J=5.0, 2.0Hz, 1H), 7.96 (dd, J=8.0, 2.0Hz, 1H), 7.23-7.28 (m, 1H), 4.44 (q, J=7.0Hz, 2H), 4.01 (br. s., 2H), 1.44 (t, J=7.0Hz, 3H).

MS (ES⁺) 229 (100%, [M+Na]⁺).

ii. 1H-Pyrido[3',2':4,5]furo[3,2-d]pyrimidine-2,4-dione, 3

Under Ar(g) and at 0° C. to a solution of compound 2 (1.189 g, 5.77 mmol) in CH₂Cl₂ (20 mL) was added dropwise chlorosulfonyl isocyanate (0.55 mL, 6.34 mmol). The reaction mixture was allowed to warm to rt, and after 4 h it was concentrated in vacuo. Water (20 mL) was added, and the suspension was stirred vigorously while heating to 70° C. for 10 min. The mixture was then cooled and filtered, washing with water. The resulting solid cake (0.87 g) was subsequently suspended in water (61 mL) and NaOH (3.15 g) was added. After 1 h stirring, LCMS analysis confirmed that the reaction had gone to completion. The mixture was then filtered, washing with water, to furnish 3 (460 mg, 2.3 mmol, 40%) as a white solid.

¹H NMR (400 MHz, DMSO-d₆) δ$_H$: 12.06 (br. s., 1H), 11.49 (br. s., 1H), 8.60 (dd, J=5.0, 1.5Hz, 1H), 8.43 (dd, J=8.0, 2.0Hz, 1H), 7.56 (dd, J=8.0, 5.0Hz, 1H).

MS (ES⁻) 202 (100%, [M−H]⁻).

iii. 2,4-Dichloro-pyrido[3',2':4,5]furo[3,2-d]pyrimidine, 4

To compound 3 (0.14 g, 0.70 mmol) and PCl₅ (2.4 g, 2.84 mmol) under Ar(g) was added POCl₃ (8 mL), and the resulting reaction mixture was then heated at reflux for 20 h. After the mixture had been cooled to rt it was poured onto crushed ice (200 mL) with vigorous stirring. The aqueous phase was then extracted with CH₂Cl₂ (3×50 mL). The combined organic layers were subsequently dried (MgSO₄) and concentrated in vacua to give 4 (66 mg, 0.28 mmol, 40%) as an off-white solid.

$^1$H NMR (400MHz, CDCl₃) $\delta_H$: 8.80 (dd, J=5.0, 1.5 Hz, 1H), 8.64 (dd, J=8.0, 2.0Hz, 1H), 7.61 (dd, J=7.5, 5.0Hz, 1H).

MS (ES⁺) 240 (100%, [M+H]⁺).

iv. 2-Chloro-4-morpholin-4-yl-pyrido[3',2':4,5]furo[3,2-d]pyrimidine, 5

To a solution of 4 (64 mg, 0.27 mmol) in dry methanol (10 mL) was added morpholine (55 μL, 0.62 mmol) dropwise, and the resulting reaction was stirred for 2 h at rt. The resulting precipitate was then filtered, washed with water and then a mixture of 5:1 methanol/water, and the remaining solid was dried in vacuo to furnish 5 (50 mg, 0.17 mmol, 64%) as a white solid.

$^1$H NMR (400 MHz, CDCl₃) $\delta_H$: 8.63 (dd, J=5.0, 2.0Hz, 1H), 8.52 (dd, J=7.5, 2.0Hz, 1H), 7.48 (dd, J=7.5, 5.0Hz, 1H), 4.10-4.23 (m, 4H), 3.86-3.91 (m, 4H).

MS (ES⁺) 291 (100%, [M−H]⁺).

v. 4-Morpholin-4-yl-2-(1H-pyrrolo[2,3-b]pyridin-4-yl)-pyrido[3',2':4,5]furo[3,2-d]pyrimidine, D Under Ar(g) to a mixture of compound 5 (20 mg, 0.069 mmol), 7-azaindole-4-boronic acid pinacol ester (18.5 mg, 0.076 mmol), dichloro-bis(triphenylphosphine)palladium (II) (2.4 mg, 0.003 mmol) and sodium hydrogen carbonate (17.4 mg, 0.21 mmol) was added ethanol (1 mL) followed by toluene (1.6 mL) and then water (0.5 mL). The reaction mixture was then heated in a microwave at 120° C. (300 W) for 1 h, and was subsequently cooled to rt; the mixture was then partitioned between CH₂Cl₂ and water, and the organic layer was separated, dried (MgSO₄) and concentrated in vacuo. Purification by flash column chromatography on silica (eluant 30-90% EtOAc/Hex) furnished D (20 mg, 0.054 mol, 78%) as an off-white solid.

$^1$H NMR (400MHz, 9:1 CDCl₃/CD₃OD) $\delta_H$: 8.61 (dd, J=7.5, 1.5Hz, 1H), 8.54 (dd, J=5.0, 1.5Hz, 1H), 8.28 (d, J=5.0Hz, 1H), 8.00 (d, J=5.0Hz, 1H), 7.46 (dd, J=7.5, 5.0Hz, 1H), 7.41 (d, J=3.5Hz, 1H), 7.32 (d, J=3.5 Hz, 1H), 4.15-4.24 (m, 4H), 3.84-3.92 (m, 4H).

MS (ES⁺) 373 (100%, [M+H]⁺).

Example E 2,8-Bis-(1H-indol-4-yl)-4-morpholin-4-yl-pyrido[3',2':4,5]furo[3,2-d]pyrimidine

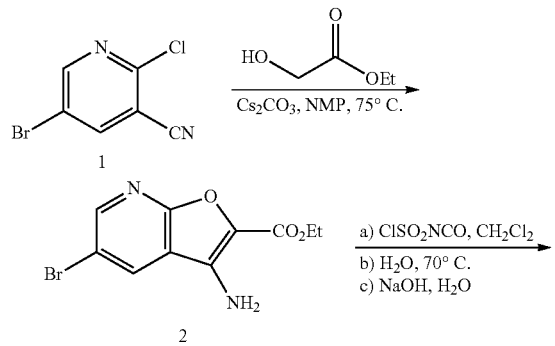

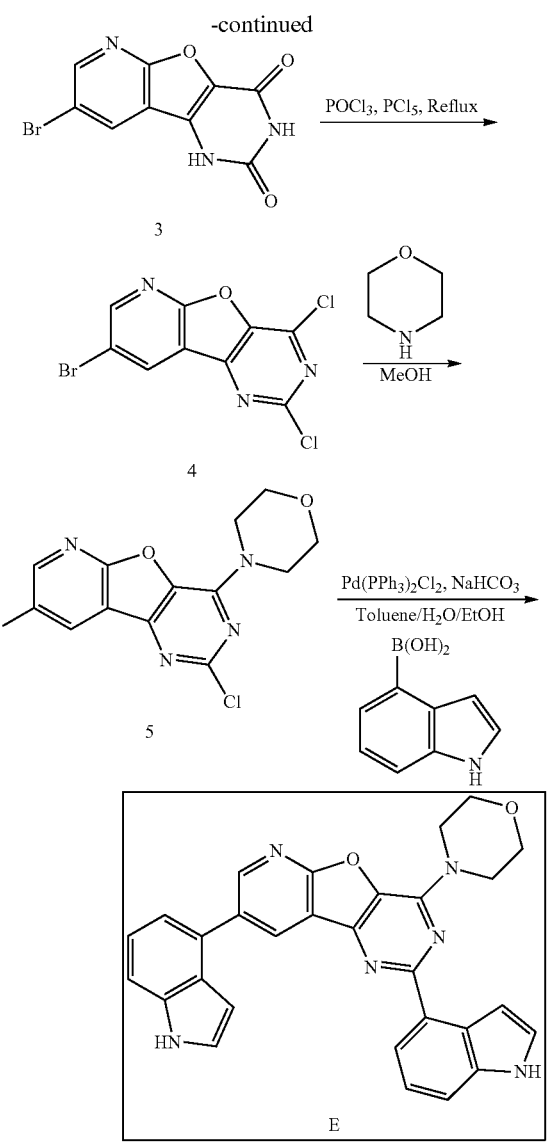

i. 3-Amino-5-bromo-furo[2,3-b]pyridine-2-carboxylic acid ethyl ester, 2

5-Bromo-2-chloro-3-pyridinecarbonitrile, 1, (4.802 g, 22.08 mmol), Cs₂CO₃ (21.6 g, 66.2 mmol) and ethyl glycolate (2.3 mL, 24.3 mmol) were placed in a flask under Ar(g). Dry NMP (50 mL) was added, and the suspension was heated at 75° C. for 20 h with vigorous stirring. The reaction mixture was cooled to rt whereupon water (200 mL) and Et₂O (3×100 mL) were added. The organic layers were combined, washed with water (3×15 mL) before being dried (MgSO₄) and concentrated in vacuo. Purification by flash column chromatography on silica (eluant 15-25% EtOAc/Hex) gave 2 (1.701 g, 5.97 mmol, 27%) as a yellow solid.

$^1$H NMR (400MHz, CDCl₃) $\delta_H$: 8.53 (d, J=2.0Hz, 1H), 8.07 (d, J=2.0Hz, 1H), 5.00 (br. s., 2H), 4.44 (q, J=7.0Hz, 2H), 1.44 (t, J=7.0Hz, 3H).

MS (ES⁻) 309 (100%, [M+Na]⁺), 307 (100%, [M+N]⁺.

ii. 8-Bromo-1H-pyrido[3',2':4,5]furo[3,2-d]pyrimidine-2,4-dione, 3

Under Ar(g) and at 0° C. to a solution of compound 2 (1.701 g, 5.97 mmol) in CH₂Cl₂ (70 mL) was added dropwise chlorosulfonyl isocyanate (0.62 mL, 7.16 mmol). The reaction mixture was allowed to warm to rt and after 2.5 h it was concentrated in vacuo. Water (140 mL) was added, and the suspension was stirred vigorously while heating to 70° C. for 1 h [MS analysis showed formation of the urea intermediate was complete]. The mixture was then cooled to rt whereupon NaOH (5.6 g [to give a 1M solution]) was added. After 25 min a yellow/white precipitate had formed, 1M HCl was added to the suspension till pH 5 was achieved whereupon the mixture was filtered, washing with water, to furnish 3 (1.418 g, 5.03 mmol, 84%) as a yellow solid.

$^1$H NMR (400 MHz, DMSO-d$_6$) $\delta_H$: 12.01 (br. s., 1H), 11.58 (br. s, 1H), 8.72 (d, J=2.0Hz, 1H), 8.59 (d, J=2.0Hz, 1H).

MS (ES$^-$) 282 (100%, [M−H]$^-$, 280 (100%, [M−H]$^-$.

iii. 2,4-Dichloro-pyrido[3',2':4,5]furo[3,2-d]pyrimidine, 4

To compound 3 (0.615 g, 2.18 mmol) and PCl$_5$ (7.2 g, 34.6 mmol) under Ar(g) was added POCl$_3$ (24 mL), and the resulting reaction mixture was then heated at reflux for 24 h. After the mixture had been cooled to rt it was poured onto crushed ice (400 mL) with vigorous stirring. The aqueous phase was then extracted with CH$_2$Cl$_2$ (3×100 mL). The combined organic layers were subsequently dried (MgSO$_4$) and concentrated in vacuo to give a 1:1 mixture of 4 and an impurity (0.532 g) as an off-white solid that was used directly in the next step.

$^1$H NMR (400MHz, CDCl$_3$) $\delta_H$: 8.78 (d, J=2.5Hz, 1H), 8.72 (d, J=2.5Hz, 1H), 8.71 (d, J=2.5Hz, 1H), 8.29 (d, J=2.5 Hz, 1H).

iv. 8-Bromo-2-chloro-4-morpholin-4-yl-pyrido[3',2':4,5]furo[3,2-d]pyrimidine, 5

To a solution of 4 (532 mg) in dry methanol (25 mL) was added morpholine (321 µL, 3.7 mmol) dropwise, and the resulting reaction was stirred for 1 h at rt. The resulting precipitate was then filtered, washed with water and dried in vacuo to furnish 5 (251 mg, 0.68 mmol, 31%, 2 steps) as a white solid.

$^1$H NMR (400MHz, CDCl$_3$) $\delta_H$: 8.66 (d, J=2.0Hz, 1H), 8.62 (d, J=2.0Hz, 1H), 4.07-4.21 (m, 4H), 3.85-3.91 (m, 4H).

MS (ES$^+$) 393 (100%, [M+Na]$^+$), 391 (80%, [M+Na]$^+$).

v. 2,8-Bis-(1H-indol-4-yl)-4-morpholin-4-yl-pyrido[3',2':4,5]furo[3,2-d]pyrimidine, E Under Ar(g) to a mixture of compound 5 (8 mg, 0.022 mmol), indole-4-boronic acid (10.5 mg, 0.065 mmol), dichloro-bis(triphenylphosphine)palladium (11) (1.5 mg, 0.002 mmol) and sodium hydrogen carbonate (8 mg, 0.097 mmol) was added ethanol (1 mL) followed by toluene (1.6 mL) and then water (0.5 mL). The reaction mixture was then heated in a microwave at 120° C. (300 W) for 1 h, and was subsequently cooled to rt; the mixture was then partitioned between CH$_2$Cl$_2$ and water, and the organic layer was separated, dried (MgSO$_4$) and concentrated in vacuo. Purification by flash column chromatography on silica (eluant 20-40% EtOAc/Hex) furnished E (2.7 mg, 0.005 mol, 25%) as a yellow solid.

$^1$H NMR (400MHz, 9:1 CDCl$_3$/CD$_3$OD) $\delta_H$: 9.08 (s, 1H), 8.88 (d, J=1.5Hz, 1H), 8.05 (d, J=7.5Hz, 1H), 7.49 (d, J=8.0 Hz, 1H), 7.43 (d, J=7.5 Hz, 1H), 7.17-7.33 (m, 6H), 6.66 (d, J=3.0Hz, 1H), 4.22-4.31 (m, 4.5 Hz, 4H), 3.85-3.95 (m, 4H).

MS (ES$^+$) 487 (100%, [M+H]$^+$).

Example F (E)-1-(4-Methyl-piperazin-1-yl)-3-[4-morpholin-4-yl-2-(1H-pyrrolo[2,3-b]pyridin-4-yl)-pyrido[3',2':4,5]furo[3,2-d]pyrimidin-8-yl]-propenone

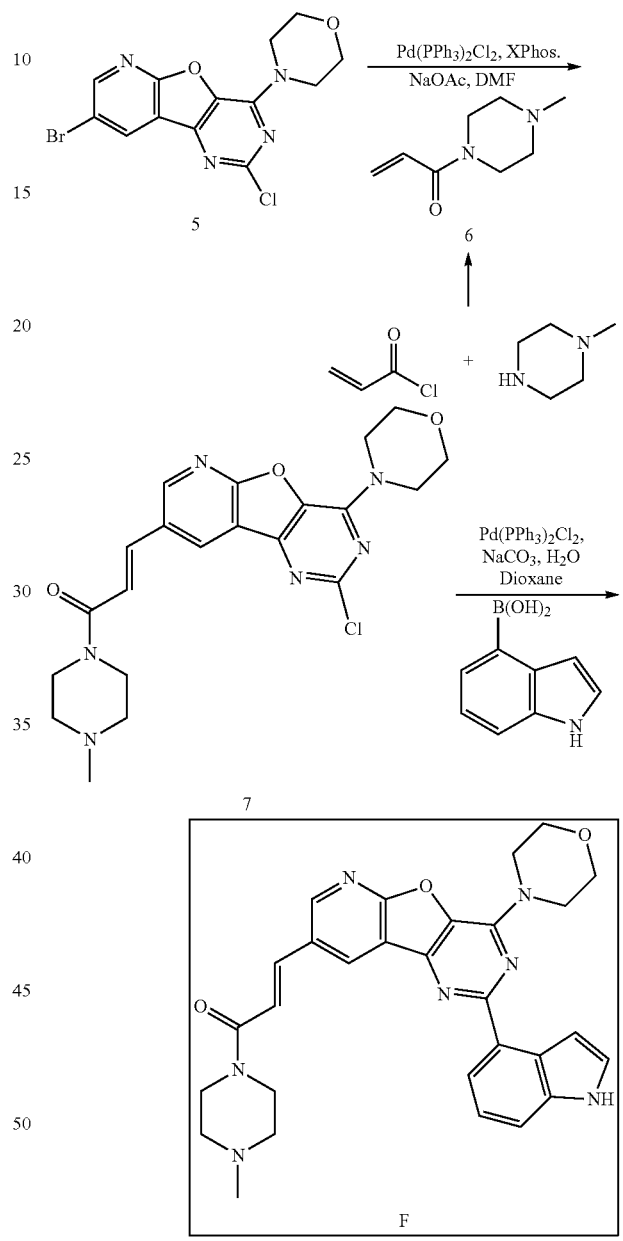

i. 1-(4-Methyl-piperazin-1-yl)-propenone, 6

At 0° C. to a solution of N-methylpiperazine (3 mL, 27 mmol) in CH$_2$Cl$_2$ (15 mL) was added acryloyl chloride (879 mL, 10.8 mmol) dropwise under Ar(g). After 2 h water (20 mL) was added. The organic layer was separated and washed with water (2×10 mL), dried (MgSO$_4$), before being concentrated in vacuo to give 6 (463 mg, 3 mmol, 28%) as a pale yellow oil that required no further purification.

$^1$H NMR (400MHz, CDCl$_3$) $\delta_H$: 6.56 (dd, J=16.6, 10.5Hz, 1H), 6.28 (dd, J=16.6, 2.0Hz, 1H), 5.61-5.75 (m, 1H), 3.54-3.79 (m, 4H), 2.38-2.49 (m, 4H), 2.33 (s, 3H).

MS (ES$^+$) 155 (100%, [M+H]$^+$).

ii. (E)-3-(2-Chloro-4-morpholin-4-yl-pyrido[3',2':4,5]furo[3,2-d]pyrimidin-8-yl)-1-(4-methyl-piperazin-1-yl)-propenone, 7

To a sealed tube was added 5 (as per Example E above, 50 mg, 0.14 mmol), 6 (20.9 mg, 0.14 mmol), dichloro-bis(triphenylphosphine)palladium (II) (2.9 mg, 0.004 mmol), XPhos (3.9 mg, 0.008 mmol) and NaOAc (33 mg, 0.41 mmol) followed by anhydrous DMF (4 mL) under Ar(g). The lid was sealed and the tube was heated to 110° C. for 16 h whereupon it was cooled to rt and diluted with EtOAc (40 mL). The organic layer was washed with water (2×20 mL); the combined aqueous layers were then extracted with $CH_2Cl_2$ (3×60 mL). The combined organic layers were then dried ($MgSO_4$) and concentrated in vacuo.

Purification by flash column chromatography on silica (eluant 2-6% MeOH/$CH_2Cl_2$) furnished 7 (44 mg, 0.10 mol, 71%) as a white solid.

$^1$H NMR (400MHz, $CDCl_3$) $\delta_H$: 8.62-8.76 (m, 2H), 7.82 (d, J=15.6Hz, 1H), 7.05 (d, J=15.6Hz, 1H), 4.07-4.23 (m, 4H), 3.85-3.92 (m, 4H), 3.68-3.84 (m, 4H), 2.47-2.61 (m, 4H), 2.39 (s, 3H).

MS (ES$^+$) 443 (100%, [M−H]$^+$).

iii. (E)-1-(4-Methyl-piperazin-1-yl)-3-[4-morpholin-4-yl-2-(1H-pyrrolo[2,3-b]pyridin-4-yl)-pyrido[3',2':4,5]furo[3,2-d]pyrimidin-8-yl]-propenone, F To a sealed tube was added 7 (20 mg, 0.045 mmol), indole-4-boronic acid (18 mg, 0.11 mmol), dichloro-bis(triphenylphosphine)palladium (II) (6.3 mg, 0.009 mmol) and $Na_2CO_3$ (9.6 mg, 0.09 mmol) followed by dioxane (2 mL) and water (0.8 mL) under Ar(g). The lid was sealed and the tube was heated to 88° C. for 20 h whereupon it was cooled to rt and diluted with EtOAc (30 mL) and 50% brine (5 mL). The organic layer was separated and the aqueous layer extracted with EtOAc (3×15 mL). The combined organic layers were then dried ($MgSO_4$) and concentrated in vacuo. Purification by flash column chromatography on silica (eluant 2-5% MeOH/$CH_2Cl_2$) furnished F (6.8 mg, 0.013 mol, 29%) as a white solid.

$^1$H NMR (400MHz, 5:1 $CDCl_3/CD_3OD$) $\delta_H$: 8.74 (d, J=2.0Hz, 1H), 8.54 (d, J=2.0Hz, 1H), 7.89 (d, J=7.5 Hz, 1H), 7.65 (d, J=15.1 Hz, 1H), 7.40 (d, J=8.0 Hz, 1H), 7.18-7.25 (m, 2H), 7.14 (t, J=7.7Hz, 1H), 7.05 (d, J=15.1 Hz, 1H), 4.08-4.13 (m, 4H), 3.75-3.82 (m, 4H), 3.61-3.73 (m, 4H), 2.37-2.55 (m, 4H), 2.27 (s, 3H).

MS (ES$^+$) 524 (100%, [M+H]$^+$).

Example G: (E)-3-[2-(1H-Indol-4-yl)-4-morpholin-4-yl-pyrido[3',2':4,5]furo[3,2-d]pyrimidin-8-yl]-N,N-dimethylacrylamide

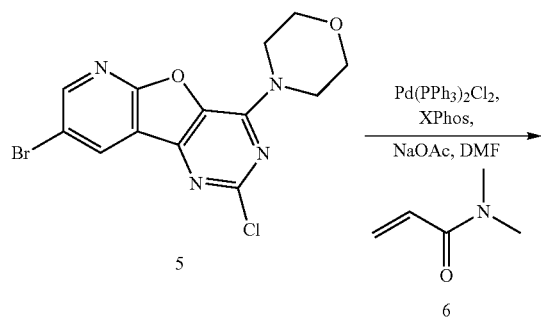

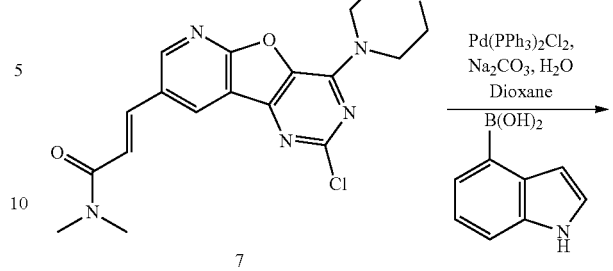

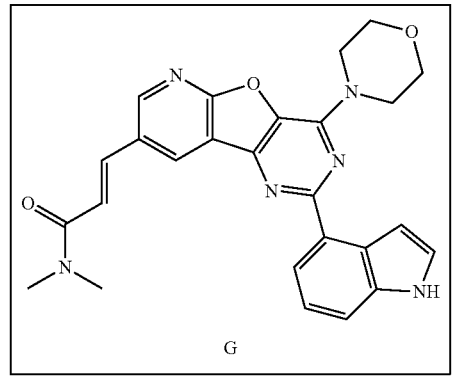

i. (E)-3-(2-Chloro-4-morpholin-4-yl-pyrido[3',2':4,5]furo[3,2-d]pyrimidin-8-yl)-N,N-dimethylacrylamide, 7

To a sealed tube was added 5 (as per Example E above, 50 mg, 0.14 mmol), dimethylacrylamide (6, 14 mL, 0.14 mmol), dichloro-bis(triphenylphosphine)palladium (II) (2.8 mg, 0.004 mmol), XPhos (3.9 mg, 0.008 mmol) and N@0/\c (33 mg, 0.41 mmol) followed by anhydrous DMF (3.5 mL) under Ar(g). The lid was sealed and the tube was heated to 110° C. for 16 h whereupon it was cooled to rt and diluted with EtOAc (40 mL). The organic layer was washed with 50% brine (3×10 mL) then dried ($MgSO_4$) and concentrated in vacuo. Purification by flash column chromatography on silica (eluant 50-100% EtOAc/Hex then 1% MeOH) furnished 7 (44 mg, 0.11 mol, 84%) as a white solid.

$^1$H NMR (400MHz, $CDCl_3$) $\delta_H$: 8.70 (s, 2H), 7.82 (d, J=15.6Hz, 1H), 7.07 (d, J=15.6Hz, 1H), 4.11-4.19 (m, 4H), 3.85-3.93 (m, 4H), 3.22 (s, 3H), 3.11 (s, 3H).

MS (ES$^+$) 388 (100%, [M+H]$^+$).

ii. (E)-3-[2-(1H-Indol-4-yl)-4-morpholin-4-yl-pyrido[3',2':4,5]furo[3,2-d]pyrimidin-8-yl]-N,N-dimethylacrylamide, G To a sealed tube was added 7 (30 mg, 0.077 mmol), indole-4-boronic acid (31 mg, 0.19 mmol), dichloro-bis(triphenylphosphine)palladium (II) (13.6 mg, 0.02 mmol) and $Na_2CO_3$ (24.4 mg, 0.23 mmol) followed by dioxane (3 mL) and water (1.2 mL) under Ar(g). The lid was sealed and the tube was heated to 88° C. for 20 h whereupon it was cooled to rt and diluted with EtOAc (30 mL) and 50% brine (3 mL). The organic layer was separated and the aqueous layer extracted with EtOAc (2×5 mL). The combined organic layers were then dried ($MgSO_4$) and concentrated in vacuo. Purification by flash column chromatography on silica (eluant 1-3% MeOH/$CH_2Cl_2$) furnished G (6.9 mg, 0.015 mol, 19%) as an off white solid.

$^1$H NMR (400MHz, 5:1 $CDCl_3/CD_3OD$) $\delta_H$: 8.77 (d, J=2.0Hz, 1H), 8.55 (d, J=2.0Hz, 1H), 7.88 (dd, J=7.5, 1.0Hz, 1H), 7.61 (d, J=15.6Hz, 1H), 7.40 (d, J=8.0Hz, 1H), 7.21 (d, J=3.0Hz, 1H), 7.10-7.17 (m, 2H), 7.04 (d, J=15.6 Hz, 1H), 4.09 (s, 4H), 3.74-3.82 (m, 4H), 3.11 (s, 3H), 2.94 (s, 3H).

MS (ES$^+$) 469 (100%, [M+H]$^+$).

Example H

[2-(1H-Indol-4-yl)-4-morpholin-4-yl-pyrido[3',2':4,5]furo[3,2-d]pyrimidin-8-ylmethyl]-dimethyl-amine

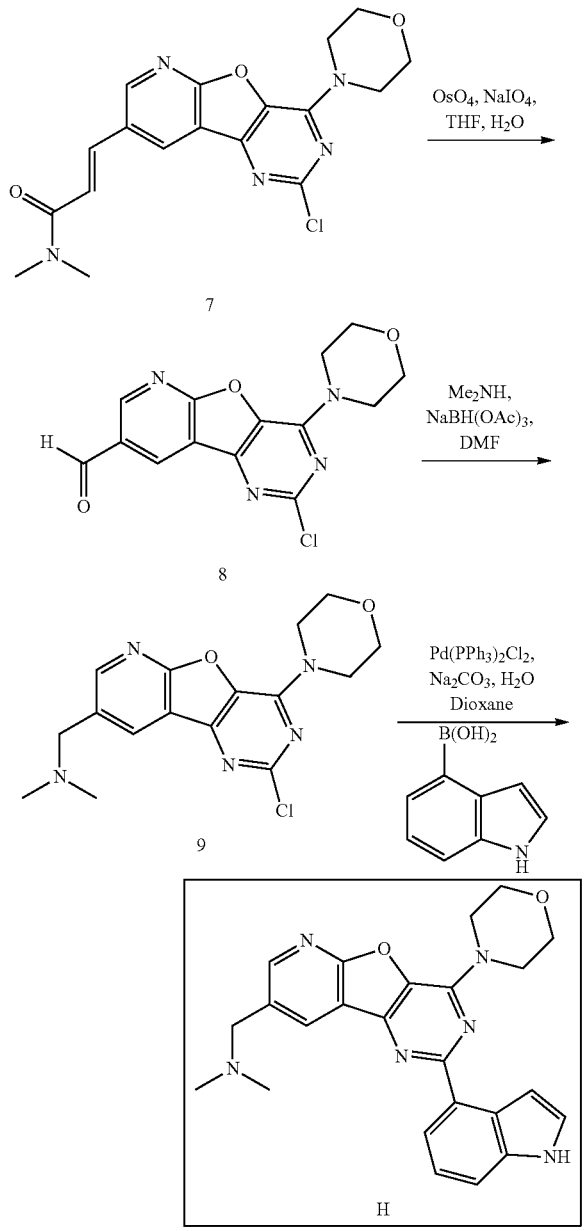

i. 2-Chloro-4-morpholin-4-yl-pyrido[3',2':4,5]furo[3,2-d]pyrimidine-8-carbaldehyde, 8

To a solution of (E)-3-(2-chloro-4-morpholin-4-yl-pyrido[3',2':4,5]furo[3,2-d]pyrimidin-8-yl)-N,N-dimethylacrylamide (7, as per Example G above) (13 mg, 0.034 mmol) in THF (1.5 mL) was added H$_2$O (0.5 mL) followed by NaIO$_4$ (22 mg, 0.10 mmol) and a solution of OsO$_4$ (2.5% wt/v in $^t$BuOH, 9 mL, 0.0009 mmol) under Ar(g). After stirring for 2 days at rt, EtOAc (25 mL) and sodium thiosulfate (0.1M, 5 mL) were added. The organic layer was separated and washed with brine (3 mL) before being dried (MgSO$_4$) and concentrated in vacuo. Purification by flash column chromatography on silica (eluant 5-20% EtOAc/CH$_2$Cl$_2$) furnished 8 (8 mg, 0.025 mmol, 74%) as a white solid.

$^1$H NMR (9:1 CDCl$_3$/CD$_3$OD) δ$_H$: 10.13 (s, 1H), 9.04 (d, J=2.0Hz, 1H), 8.91 (d, J=2.0Hz, 1H), 3.99-4.13 (m, 4H), 3.73-3.84 (m, 4H).

LCMS (ES$^+$) 351 (100%, [M+MeOH+H]$^+$), 319 (40%, [M+H]$^+$).

ii. (2-Chloro-4-morpholin-4-yl-pyrido[3',2':4,5]furo[3,2-d]pyrimidin-8-ylmethyl)-dimethyl-amine, 9

To a suspension of 8 (7.8 mg, 0.024 mmol) in dry DMF (2.5 mL) was added a solution of dimethylamine (2M in MeOH, 24 mL, 0.049 mmol) followed by NaBH(OAc)$_3$ (8 mg, 0.037 mmol) under Ar(g). After stirring at rt for 23 h, a further quantity of dimethylamine (2M in MeOH, 35 mL, 0.071 mmol) and NaBH(OAc)$_3$ (6 mg, 0.028 mmol) were added. After 3 days the reaction was concentrated in vacua. EtOAc (40 mL) and 50% saturated brine (5 mL) were added and the organic layer separated, re-extracting the aqueous with EtOAc (2×15 mL). The combined organic layers were then dried (MgSO$_4$) and concentrated in vacuo. Purification by flash column chromatography on silica (eluant 1-6% MeOH/CH$_2$Cl$_2$) furnished 9 (5 mg, 0.014 mmol, 60%) as a white solid.

$^1$H NMR (CDCl$_3$) δ$_H$: 8.65 (d, J=2.0Hz, 1H), 8.50 (d, J=2.0Hz, 1H), 4.08-4.23 (m, 4H), 3.82-3.93 (m, 4H), 3.75 (br. s., 2H), 2.38 (s, 6H).

MS (ES$^+$) 348 (100%, [M+H]$^+$).

iii. [2-(1H-Indol-4-yl)-4-morpholin-4-yl-pyrido[3',2':4,5]furo[3,2-d]pyrimidin-8-ylmethyl]-dimethyl-amine, H To a sealed tube was added 9 (5 mg, 0.014 mmol), indole-4-boronic acid (5.8 mg, 0.036 mmol), dichloro-bis(triphenylphosphine)palladium (II) (2.0mg, 0.0029 mmol) and Na$_2$CO$_3$ (3.1 mg, 0.029 mmol) followed by dioxane (2 mL) and water (0.8 mL) under Ar(g). The lid was sealed and the tube was heated to 88° C. for 18 h whereupon it was cooled to rt and diluted with EtOAc (35 mL) and 50% saturated brine (5 mL). The organic layer was separated and the aqueous layer extracted with EtOAc (2×10 mL). The combined organic layers were then dried (MgSO$_4$) and concentrated in vacuo. Purification by flash column chromatography on silica (eluant 2-5% MeOH/CH$_2$Cl$_2$) furnished H (2 mg, 0.005 mmol, 32%) as an off-white solid.

$^1$H NMR (400MHz, 9:1 CDCl$_3$/CD$_3$OD) δ$_H$: 9.79 (br. s., 1H), 8.57 (br. s, 1H), 8.53 (br. s., 1H), 7.98 (d, J=7.5Hz, 1H), 7.45 (d, J=8.0Hz, 1H), 7.24-7.32 (m, 2H), 7.19 (t, J=8.0Hz, 1H), 4.13-4.19 (m, 4H), 3.81-3.87 (m, 4H), 3.78 (br. s, 2H), 2.36 (s, 6H).

MS (ES$^+$) 429 (100%, [M+H]$^+$).

Example I 2-(1H-Indol-4-yl)-4-morpholin-4-yl-8-piperidin-1-ylmethyl-pyrido[3',2':4,5]furo[3.2d]pyrimidine

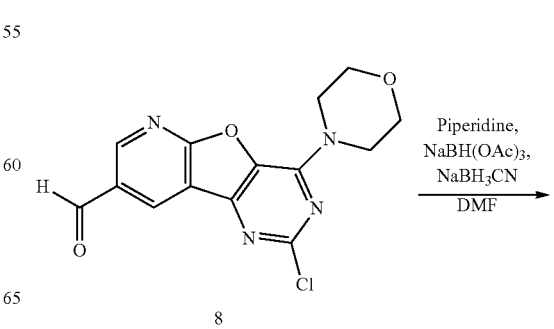

-continued

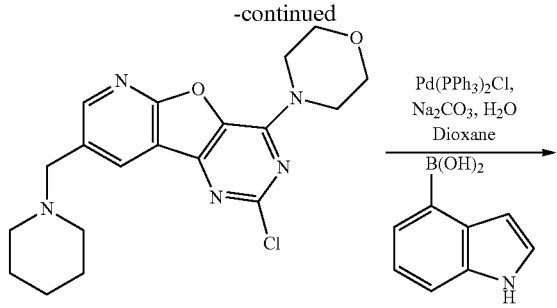

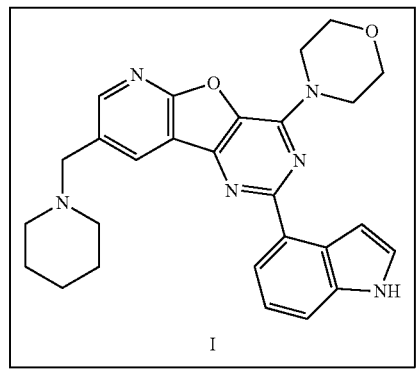

i. 2-Chloro-4-morpholin-4-yl-8-piperidin-1-ylmethyl-pyrido[3',2':4,5]furo[3,2-d]pyrimidine, 10

To compound 8 (as per Example H above) (19.7 mg, 0.062 mmol in dry DMF (6.3 mL) was added piperidine (12.2 μL, 0.14 mmol) followed by NaBH(OAc)$_3$ (20.05 mg, 0.095 mmol) and the reaction was stirred for 5 h. After which time NaBH$_3$CN (5.8 mg, 0.092 mmol) was added and the reaction was stirred for a further 48 h. The DMF was removed in vacuo, EtOAc (50 mL) was added along with 50% saturated brine (50 mL), the layers separated, extracted with EtOAc (2×30 mL), dried (MgSO$_4$) and concentrated in vacuo. Purification by flash column chromatography on silica (eluant 0:1-6:94) MeOH/CH$_2$Cl$_2$) furnished 10 (12.9 mg, 0.033 mmol, 54%) as a white solid.

$^1$H NMR (400MHz, CDCl$_3$) $\delta_H$: 8.55 (d, J=2.0Hz, 1H), 8.49 (d, J=2.0Hz, 1H), 4.15 (br. s., 4H), 3.84-3.90 (m, 4H), 3.65 (s, 2H), 2.42 (m, 4H), 1.59 (quin, J=5.5Hz, 4H), 1.41-1.49 (m, 2H).

MS (ES$^+$) 388.2 (100%, [M+H]$^+$).

ii. 2-(1H-Indol-4-yl)-4-morpholin-4-yl-8-piperidin-1-ylmethyl-pyrido[3',2':4,5]furo[3,2d]pyrimidine, I To indole-4-boronic acid (13.4 mg, 0.083 mmol), dichlorobis(triphenylphosphine)palladium (II) (4.60 mg, 0.0065 mmol) and sodium carbonate (7.22 mg, 0.068 mmol) was added compound 10 (12.9 mg, 0.033 mmol) dissolved in dioxane/water (2 mL/0.8 mL). The reaction was than heated in a sealed tube at 88° C. for 16 h. The reaction was cooled to rt where the reaction was partitioned between EtOAc/water (30 mL/5 mL) and the layers were separated, extracted with EtOAc (3×10 mL), dried (MgSO$_4$) and concentrated in vacuo. Purification by flash column chromatography on silica (eluant 0:1-6:94) MeOH/CH$_2$Cl$_2$) give I (4 mg, 0.0085 mol, 26%) as a white solid.

$^1$H NMR (400MHz, 9.5:0.5 CDCl$_3$/CD$_3$OD) $\delta_H$: 8.59 (d, J=2.0Hz, 1H), 8.50 (d, J=2.5Hz, 1H), 8.12 (d, J=7.5Hz, 1H), 7.49 (d, J=8.0 Hz, 1H), 7.45-7.47 (m, 1H), 7.33 (d, J=3.0Hz, 1H), 7.25-7.30 (m, 2H), 4.22 (t, J=4.9Hz, 4H), 3.87-3.92 (m, 4H), 3.67 (s, 2H), 2.44 (m, 4H), 1.54-1.62 (m, 4H), 1.39-1.46 (m, 2H).

MS (ES$^+$) 469.2 (100%, [M+H]$^+$).

Example J 2-(1H-Indol-4-yl)-8-(4-methyl-piperazin-1-ylmethyl)-4-morpholin-4-yl-pyrido[3',2':4,5]furo[3,2-d]pyrimidine

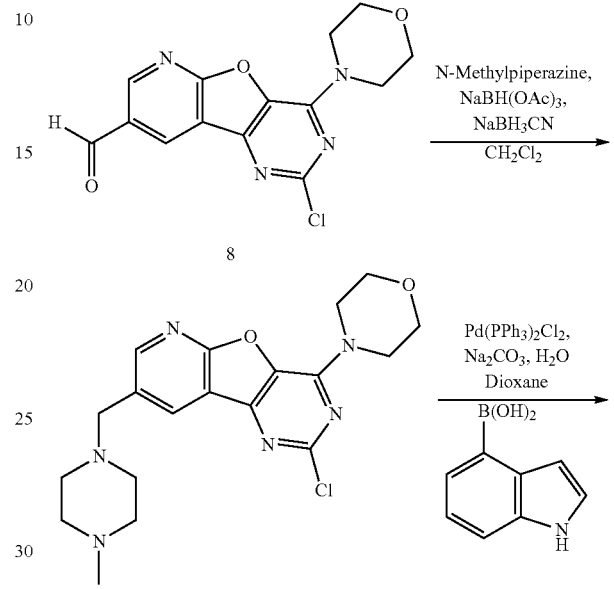

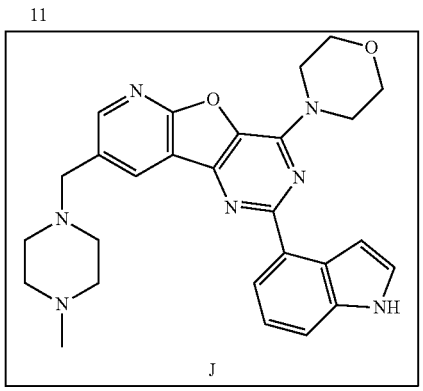

i. 2-Chloro-8-(4-methyl-piperazin-1-ylmethyl)-4-morpholin-4-yl-pyrido[3',2':4,5]furo[3,2-d]pyrimidine, 11

To compound 8 (as per Example H above) (19.13 mg, 0.060 mmol) in dry CH$_2$Cl$_2$ (6.6 mL) was added N-methylpiperazine (13.3 μL, 0.12 mmol) followed by NaBH$_3$CN (4.6 mg, 0.073 mmol) and the reaction mixture was stirred for 21 h. NaBH(OAc)$_3$ (11.3 mg, 0.053 mmol) was then added and the reaction mixture was stirred for a further 6.5 h. EtOAc (50 mL) was added along with 50% saturated brine (50 mL); the layers were separated, extracted with EtOAc (2×30 mL), dried over MgSO$_4$, and concentrated in vacuo. Purification by flash column chromatography on silica (eluant 0:1-1:9 MeOH/CH$_2$Cl$_2$) furnished 11 (8.48 mg, 0.021 mmol, 35%) as a white solid.

$^1$H NMR (400MHz, 9:1 CDCl$_3$/CD$_3$OD) $\delta_H$: 8.49 (d, J=2.5Hz, 1H), 8.45 (d, J=2.0Hz, 1H), 4.10 (br. s., 4H), 3.82 (t, J=4.8Hz, 4H), 3.65 (s, 2H), 2.49 (br. s., 8H), 2.27 (s, 3H). MS (ES$^+$) 403.1 (100%, [M+H]$^+$).

ii. 2-(1H-Indol-4-yl)-8-(4-methyl-piperazin-1-ylmethyl)-4-morpholin-4-yl-pyrido[3',2':4,5]furo[3,2-d]pyrimidine, J To indole-4-boronic acid (14.1 mg, 0.088 mmol), dichlorobis(triphenylphosphine)palladium (II) (4.77 mg, 0.0068 mmol) and sodium carbonate (7.47 mg, 0.070 mmol) was added compound 11 (13.1 mg, 0.032 mmol) dissolved in dioxane/water (2 mL/0.8 mL). The resulting reaction mixture was then heated in a sealed tube at 88° C. for 16 h. The mixture was then cooled to rt, and was partitioned between EtOAc/water (30 mL/5 mL); the layers were subsequently separated, extracted with EtOAc (2×10 mL), dried (MgSO$_4$) and concentrated in vacuo. Purification by flash column chromatography on silica (eluant 0:1-1:9) MeOH/CH$_2$Cl$_2$) furnished compound J (3.97 mg, 0.0082 mol, 25%) as a white solid.

$^1$H NMR (400MHz, 9:1 CDCl$_3$/CD$_3$OD) $\delta_H$: 8.59 (d, J=2.0Hz, 1H), 8.48 (d, J=2.0Hz, 1H), 8.06-8.12 (m, 1H), 7.48 (d, J=8.0Hz, 1H), 7.42 (d, J=3.0Hz, 1H), 7.32 (d, J=3.0Hz, 1H), 7.25 (s, 1H), 4.20 (t, J=4.8 Hz, 4H), 3.88 (m, J=4.8 Hz, 4H), 3.67 (s, 2H), 2.51 (br. s., 8H), 2.25 (s, 3H).

MS (ES$^+$) 484.2 (100%, [M+H]$^+$).

Example K 2-(1H-Indol-4-yl)-4-morpholin-4-yl-8-morpholin-4-ylmethyl-pyrido[3',2':4,5]furo[3,2-d]pyrimidine

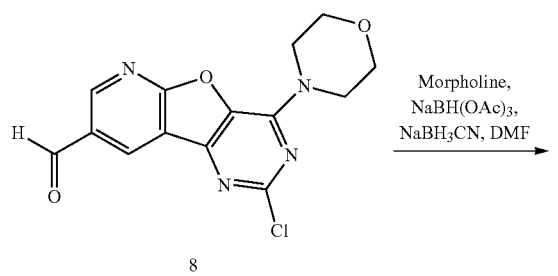

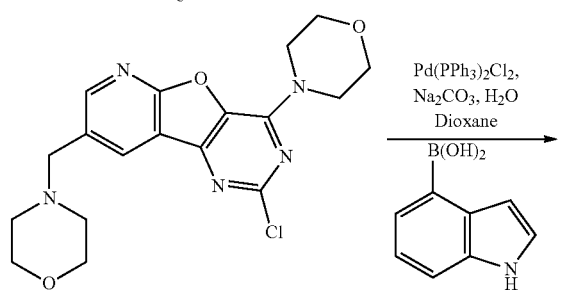

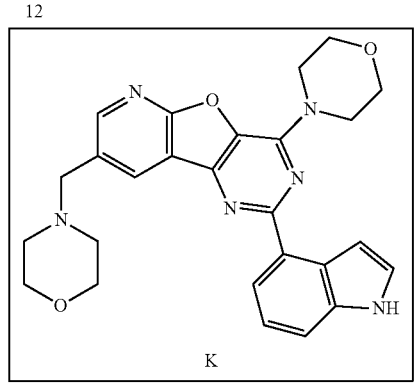

i. 2-Chloro-4-morpholin-4-yl-8-morpholin-4-ylmethyl-pyrido[3',2':4,5]furo[3,2-d]pyrimidine, 12

To compound 8 (as per Example H above) (19.7 mg, 0.062 mmol) in dry DMF (3 mL) was added morpholine (11 μL, 0.13 mmol) followed by NaBH(OAc)$_3$ (20 mg, 0.095 mmol) under Ar(g) and the reaction mixture was stirred for 3 days. NaBH$_3$CN (5 mg, 0.07 mmol) was then added, and the reaction mixture was stirred for a further 5 h. The DMF was then removed in vacuo, and EtOAc (40 mL) was added along with 50% saturated brine (5 mL); the resulting layers were separated, extracted with EtOAc (2×15 mL), dried (MgSO$_4$) and concentrated in vacuo. Purification by flash column chromatography on silica (eluant 1-2.5% MeOH/CH$_2$Cl$_2$) furnished 12 (15 mg, 0.038 mmol, 61%) as a white solid.

$^1$H NMR (CDCl$_3$) $\delta_H$: 8.56 (s, 1H), 8.53 (s, 1H), 4.08-4.21 (m, 4H), 3.83-3.91 (m, 4H), 3.65-3.79 (m, 6H), 2.43-2.59 (m, 4H).

MS (ES$^+$) 390 (100%, [M+H]$^+$).

ii. 2-(1H-Indol-4-yl)-4-morpholin-4-yl-8-morpholin-4-ylmethyl-pyrido[3',2':4,5]furo[3,2-d]pyrimidine, K To a sealed tube was added compound 12 (15 mg, 0.038 mmol), indole-4-boronic acid (15.5 mg, 0.1 mmol), dichlorobis(triphenylphosphine)palladium (II) (5.4 mg, 0.008 mmol) and Na$_2$CO$_3$ (8.2 mg, 0.077 mmol), followed by dioxane (2 mL) and water (0.8 mL) under Arg). The tube was heated to 88° C. for 18 h whereupon it was cooled to rt, and diluted with EtOAc (35 mL) and 50% saturated brine (5 mL). The organic layer was separated and the aqueous layer extracted with EtOAc (2×10 mL). The combined organic layers were then dried (MgSO$_4$) and concentrated in vacuo. Purification by flash column chromatography on silica (eluant 1-3% MeOH/CH$_2$Cl$_2$) furnished K (6.7 mg, 0.014 mmol, 37%) as an off-white solid.

$^1$H NMR (400MHz, CDCl$_3$) $\delta_H$: 8.63 (d, J=2.0Hz, 1H), 8.58 (br. s., 1H), 8.39 (br. s., 1H), 8.24 (dd, J=7.5, 1.0Hz, 1H), 7.58-7.67 (m, 1H), 7.53 (d, J=8.0Hz, 1H), 7.38 (t, J=2.5Hz, 1H), 7.34 (t, J=8.0Hz, 1H), 4.19-4.33 (m, 4H), 3.90-4.01 (m, 4H), 3.67-3.84 (m, 6H), 2.45-2.67 (m, 4H).

MS (ES$^+$) 471 (100%, [M−H]$^+$).

Example L

[2-(1H-Indol-4-yl)-4-morpholin-4-yl-pyrido[3',2':4,5]furo[3,2-d]pyrimidin-8-ylmethyl]-(2-methoxyethyl)-methyl-amine

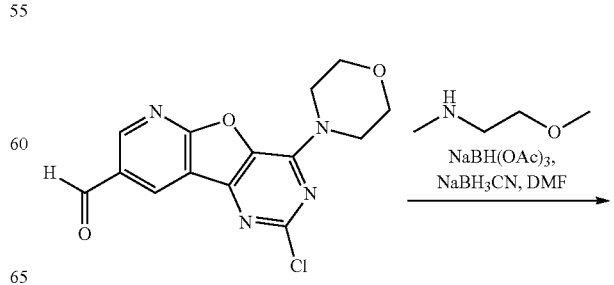

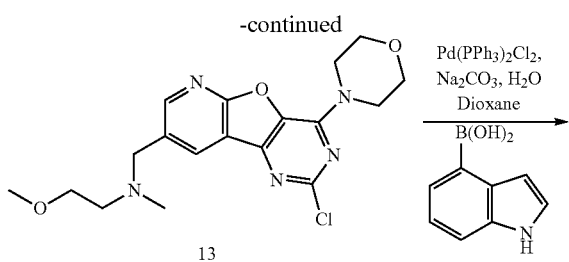

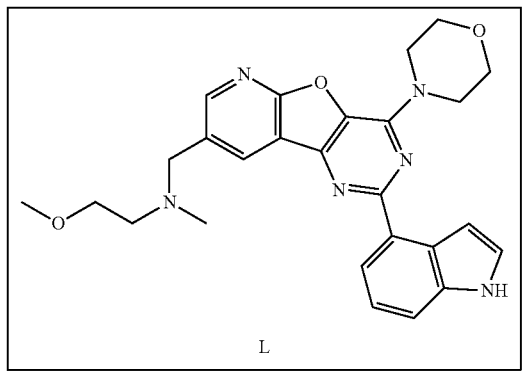

i. (2-Chloro-4-morpholin-4-yl-pyrido[3',2':4,5]furo[3,2-d]pyrimidin-8-ylmethyl)-(2-methoxy-ethyl)-methyl-amine, 13

To compound 8 (as per Example H above) (23 mg, 0.072 mmol) in dry CH$_2$Cl$_2$ (5 mL), MeOH (2 mL) was added 3 Å molecular sieves, (2-methoxyethyl)methylamine (12 μL, 0.11 mmol) followed by NaBH(OAc)$_3$ (46 mg, 0.22 mmol) and NaBH$_3$CN (4.5 mg, 0.07 mmol) under Ar(g). After 18 h, the reaction mixture was filtered, washing through with CH$_2$Cl$_2$ (30 mL). 50% saturated brine (5 mL) was then added to the filtrate and the layers were separated, extracting with CH$_2$Cl$_2$ followed by EtOAc, dried (MgSO$_4$) and concentrated in vacuo. Purification by first flash column chromatography on silica (eluant 1-4% MeOH/CH$_2$Cl$_2$) followed by ion exchange column chromatography (SCX-3, MeOH-0.5M NH$_3$ in MeOH) furnished 13 (11 mg, 0.028 mmol, 39%) as a white solid.

$^1$H NMR (400MHz, CDCl$_3$) δ$_H$: 8.60 (d, J=2.0Hz, 1H), 8.49 (d, J=2.0Hz, 1H), 4.10-4.19 (m, 4H), 3.84-3.90 (m, 4H), 3.80 (br. s., 2H), 3.57 (t, J=5.5Hz, 2H), 3.37 (s, 3H), 2.71 (t, J=5.5 Hz, 2H), 2.31 (s, 3H).

MS (ES$^+$) 392 (100%, [M+H]$^+$).

ii. [2-(1H-Indol-4-yl)-4-morpholin-4-yl-pyrido[3',2':4,5]furo[3,2-d]pyrimidin-8-ylmethyl]-(2-methoxy-ethyl)-methyl-amine, L To a sealed tube was added compound 13 (11 mg, 0.028 mmol), indole-4-boronic acid (11.3 mg, 0.07 mmol), dichloro-bis(triphenylphosphine)palladium (II) (4 mg, 0.006 mmol) and Na$_2$CO$_3$ (6 mg, 0.056 mmol) followed by dioxane (2 mL) and water (0.8 mL) under Ar(g). The tube was heated to 88° C. for 18 h whereupon it was cooled to rt and diluted with EtOAc (35 mL) and 50% saturated brine (5 mL). The organic layer was separated and the aqueous layer extracted with EtOAc (2×10 mL). The combined organic layers were then dried (MgSO$_4$) and concentrated in vacuo. Purification by flash column chromatography on silica (eluant 1-3% MeOH/CH$_2$Cl$_2$) furnished L (4.5 mg, 0.01 mmol, 34%) as an off-white solid.

$^1$H NMR (400MHz, 9:1 CDCl$_3$/CD$_3$OD) δ$_H$: 9.80 (br. s., 1H), 8.56 (s, 1H), 8.49 (br. s., 1H), 7.98 (d, J=7.5Hz, 1H), 7.44 (d, J=8.0Hz, 1H), 7.31 (br. s., 1H), 7.24-7.28 (m, 1H), 7.18 (t, J=7.5Hz, 1H), 4.10-4.20 (m, 4H), 3.76-3.87 (m, 4H), 3.51 (t, J=5.0Hz, 2H), 3.27 (s, 3H), 3.22-3.26 (m, 2H), 2.59-2.75 (m, 2H), 2.29 (s, 3H).

MS (ES$^+$) 473 (100%, [M+H]$^+$).

Example M 2-(1H-Indol-4-yl)-4,8-di-morpholin-4-yl-pyrido[3',2':4,5]furo[3,2-d]pyrimidine

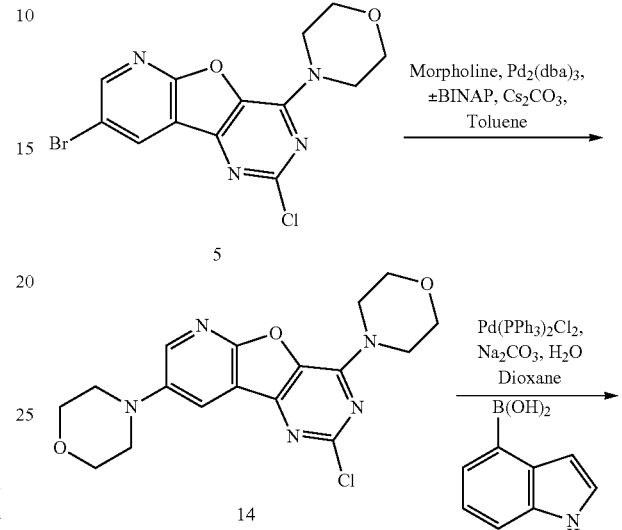

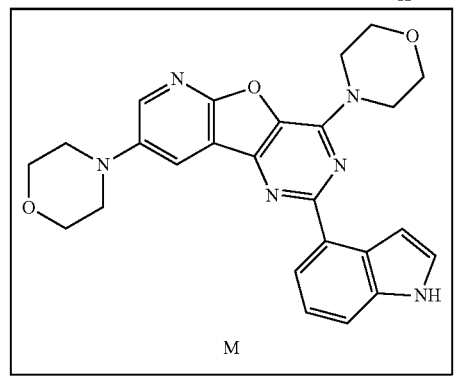

i. 2-Chloro-4,8-di-morpholin-4-yl-pyrido[3,2':4,5]furo[3,2-d]pyrimidine, 14

To a sealed tube was added compound 5 (as per Example E above, 20 mg, 0.054 mmol), Pd$_2$(dba)$_3$ (1.5 mg, 0.0016 mmol), ±BINAP (2 mg, 0.0032 mmol) and Cs$_2$CO$_3$ (26 mg, 0.081 mmol) followed by dry toluene (2 mL) and morpholine (5.7 mL, 0.065 mmol) under Ar(g). The tube was heated at 90° C. for 18 h. After cooling to rt, EtOAc (35 mL) and 50% saturated brine (5 mL) were added. The organic layer was separated and the aqueous layer extracted with EtOAc (2×10 mL). The combined organic layers were then dried (MgSO$_4$) and concentrated in vacuo. Purification by flash column chromatography on silica (eluant 0.5-2% MeOH/CH$_2$Cl$_2$) furnished 14 (10 mg, 0.027 mmol, 49%) as a yellow solid.

$^1$H NMR (400MHz, CDCl$_3$) δ$_H$: 8.34 (d, J=3.0Hz, 1H), 7.94 (d, J=3.0Hz, 1H), 4.07-4.23 (m, 4H), 3.90-3.97 (m, 4H), 3.81-3.89 (m, 4H), 3.18-3.28 (m, 4H).

MS (ES$^+$) 376 (100%, [M+H]$^+$).

ii. 2-(1H-Indol-4-yl)-4,8-di-morpholin-4-yl-pyrido[3',2':4,5]furo[3,2-d]pyrimidine, M To a sealed tube was added compound 14 (10 mg, 0.027 mmol), indole-4-boronic acid (10.9 mg, 0.068 mmol), dichloro-bis(triphenylphosphine)palladium (II) (3.7 mg, 0.005 mmol) and $Na_2CO_3$ (5.7 mg, 0.054 mmol) followed by dioxane (2 mL) and water (0.8 mL) under Ar(g). The tube was heated to 88° C. for 18 h whereupon it was cooled to rt and diluted with EtOAc (35 mL) and 50% saturated brine (5 mL). The organic layer was separated and the aqueous layer extracted with EtOAc (2×10 mL). The combined organic layers were then dried ($MgSO_4$) and concentrated in vacuo. Purification by first flash column chromatography on silica (eluant 0.5-1.5% $MeOH/CH_2Cl_2$) followed by ion exchange column chromatography (SCX-3, MeOH-0.5M $NH_3$ in MeOH) furnished M (3.2 mg, 0.007 mmol, 26%) as a white solid.

$^1$H NMR (400MHz, $CDCl_3$) $\delta_H$: 8.39 (br. s., 1H), 8.35 (d, J=2.5Hz, 1H), 8.21 (d, J=7.5Hz, 1H), 7.33-7.58 (m, 3H), 7.19-7.31 (m, 2H), 4.19-4.37 (m, 4H), 3.85-4.02 (m, 8H), 3.25-3.37 (m, 4H).

LCMS (ES$^+$) 457 (100%, [M+H]$^+$).

Example N 2-(1H-Indol-4-yl)-7-methyl-4-morpholin-4-yl-pyrido[3',2':4,5]furo[3,2-d]pyrimidine i. 3-Amino-6-methyl-furo[2,3-b]pyridine-2-carboxyl(c acid ethyl ester, 16

To a suspension of 2-chloro-3-cyano-6-methylpyridine, 15 (2.0g, 13.1 mmol, 1 eq) and cesium carbonate (12.8 g, 39.3 mmol, 3 eq) in anhydrous NMP (20 mL) was added at rt ethyl glycolate (1.36 mL, 14.4 mmol, 1.1 eq) under Ar/g). The reaction mixture was heated up at 75° C. overnight; once cooled down, it was partitioned with $H_2O$ (200 mL) and extracted with EtOAc (3×70 mL). The combined organics were thoroughly washed with $H_2O$ (3×75 mL), then dried over $MgSO_4$ and the solvent was removed in vacuo. The residue was further purified by silica gel column chromatography with hexane/EtOAc (4:1-1:3) to yield 16 as a pale yellow solid (1.30 g, 45%).

$^1$H NMR (400MHz, $CDCl_3$) $\delta_H$: 7.84 (d, J=8.0Hz, 1H), 7.12 (d, J=8.0Hz, 1H), 4.41 (q, J=7.0Hz, 2H), 4.26 (br. s., 2H), 2.66 (s, 3H), 1.42 (t, J=7.0 Hz, 3H).

MS (ES$^+$) 221.0 (50%, [M+H]$^+$), 243.0 (50%, [M+Na]$^+$).

ii. 7-Methyl-1H-pyrido[3',2':4,5]furo[3,2-d]pyrimidine-2,4-dione, 17

A round-bottomed flask was loaded up with 3-amino-6-methyl-furo[2,3-d]pyridine-2-carboxylic acid ethyl ester, 16 (926 mg, 4.20 mmol, 1 eq) and urea (2.52 g, 42.0mmol, 10 eq). The mixture was heated up at 190° C. for 3 h until no

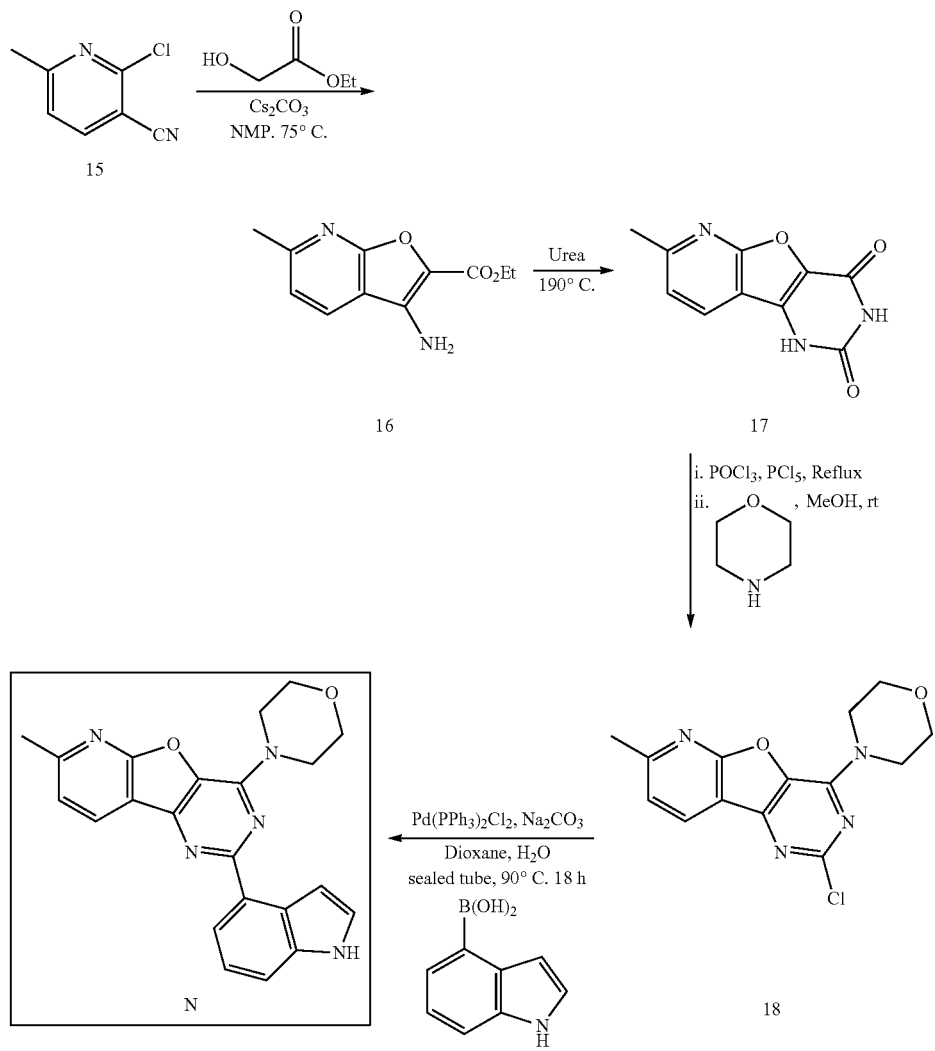

more ammonia release was observed. H₂O (10 mL) was added, and the reaction mixture was stirred for 30 min vigorously; it was then filtered, and the solid was washed with H₂O (3×10 mL) before drying to furnish the product as a pale brown solid (1.60 g, quant.)

¹H NMR (400MHz, DMSO-d₆) δ_H: 8.24 (d, J=7.5Hz, 1H), 7.40 (d, J=8.0 Hz, 1H), 7.16 (br. s., 1H), 5.41 (br. s., 1H), 2.61 (s, 3H).

MS (ES⁺) 240.0 (100%, [M+Na]⁺).

iii. 2-Chloro-7-methyl-4-morpholin-4-yl-pyrido[3',2':4,5]furo[3,2-d]pyrimidine, 18

To a mixture of 7-methyl-1H-pyrido[3',2':4,5]furo[3,2-d]pyrimidine-2.4-dione (1.6 g, 4.20 mmol, 1 eq) 17, and PCl₅ (10.5 g, 50 mmol, 12 eq) was added at rt POCl₃ (33.5 mL, 357 mmol, 85 eq) under Ar(g). The reaction mixture was refluxed at 115° C. overnight. Once cooled down to rt, the mixture was poured dropwise very slowly onto stirred crushed ice over 2 h, then warmed up to rt for 1 h. The resulting aqueous was extracted with EtOAc (3×100 mL) and CH₂Cl₂ (4×100 mL). The combined organics were dried over MgSO₄ and the solvent was removed in vacuo. To this residue in dry MeOH (50 mL) was added at rt morpholine (0.92 mL, 10.5 mmol, 2.5 eq) under Ar(g). The reaction mixture was stirred for 3 h, then the solvent was removed in vacuo. The residue was further purified by silica gel column chromatography with hexane/EtOAc (1:1-0:1) to yield the product as a pale brown solid (384 mg, 30%).

¹H NMR (400MHz, CDCl₃) δ_H: 8.38 (d, J=8.0Hz, 1H), 7.34 (d, J=8.0Hz, 1H), 4.10-4.19 (m, 4H), 3.84-3.89 (m, 4H), 2.74 (s, 3H).

MS (ES⁺) 305.0(90%, [M−H]⁺).

iv. 2-(1H-Indol-4-yl)-7-methyl-4-morpholin-4-yl-pyrido[3',2':4,5]furo[3,2-d]pyrimidine, N To a solution of 2-chloro-7-methyl-4-morpholin-4-yl-pyrido[3',2':4,5]furo[3,2-d]pyrimidine, 18 (27 mg, 0.09 mmol, 1eq), indole-4-boronic acid (43 mg, 0.27 mmol, 3 eq) and PdCl₂(PPh₃)₂ (12.4 mg, 0.02 mmol, 20 mol%) in a mixture of dioxane (2 mL) and H₂O (1.0 mL) was added Na₂CO₃ (19 mg, 0.18 mmol, 2 eq) under Ar(g). The reaction mixture was then heated in a pressure tube for 18 h at 90° C. Once cooled down, the mixture was partitioned with H₂O (10 mL) and extracted with CH₂Cl₂ (2×10 mL) and EtOAc (2×10 mL). The combined organic extracts were dried over MgSO₄ and the solvent was removed in vacuo. The residue was further purified by SCX-3 cartridge eluting with CH₂Cl₂/MeOH (1:0-0:1 then +1M NH₃) followed by silica gel column chromatography with hexane/EtOAc (3:1-0:1) to yield N as a pale brown solid (5.4 mg, 16%).

¹H NMR (400MHz, CDCl₃+10% MeOD) δ_H: 8.38 (d, J=8.0 Hz, 1H), 7.82 (d, J=7.5Hz, 1H), 7.35 (d, J=8.0Hz, 1H), 7.19 (d, J=7.5Hz, 1H), 7.16 (d, J=3.0Hz, 1H), 7.12 (m, J=1.0Hz, 1H), 7.08 (t, J=7.5Hz, 1H), 4.03-4.09 (m, 4H), 3.70-3.76 (m, 4H), 2.54 (s, 3H).

MS (ES⁺) 386.1 (100%, [M+H]⁺).

Example O 8-(4-Fluoro-piperidin-1-ylmethyl)-2-(1H-indol-4-yl)-4-morpholin-4-yl-pyrido[3',2':4,5]furo[3,2-d]pyrimidine

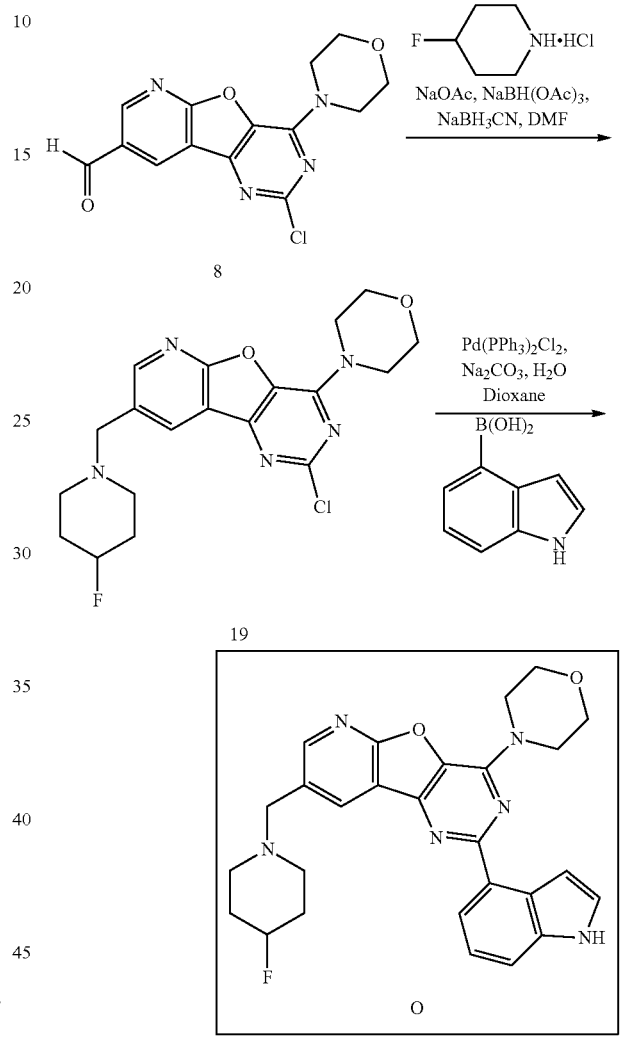

i. 2-Chloro-8-(4-fluoro-piperidin-1-ylmethyl)-4-morpholin-4-yl-pyrido[3',2':4,5]furo[3,2-d]pyrimidine, 19

To compound 8 (as per Example H above) (80 mg, 0.25 mmol) in dry DMF (12 mL) was added 4-fluoropiperidine hydrochloride (70 mg, 0.5 mmol) and NaOAc (41 mg, 0.5 mmol) under Ar(g). After 20 minutes NaBH(OAc)₃ (106 mg, 0.5 mmol) and NaBH₃CN (16 mg, 0.25 mmol) were added and the suspension was stirred for 16 h. The DMF was then removed in vacuo, EtOAc (45 mL) was added along with 50% saturated brine (7 mL), the layers separated, extracted with EtOAc (2×15 mL), dried (MgSO₄) and concentrated in vacuo. Purification by flash column chromatography on silica (eluant 1-2% MeOH/CH₂Cl₂) furnished 9 (58 mg, 0.014 mmol, 57%) as a white solid.

¹H NMR (300MHz, CDCl₃) δ_H: 8.55 (d, J=1.8Hz, 1H), 8.51 (d, J=1.8Hz, 1H), 4.58-4.86 (m, 1H), 4.06-4.23 (m, 4H), 3.82-3.92 (m, 4H), 3.69 (s, 2H), 2.54-2.68 (m, 2H), 2.38-2.52 (m, 2H), 1.81-2.00 (m, 4H).

LCMS (ES⁺) 406 (100%, [M−H]⁺).

ii. 8-(4-Fluoro-piperidin-1-ylmethyl)-2-(1H-indol-4-yl)-4-morpholin-4-yl-pyrido[3',2':4,5]furo[3,2-d]pyrimidine, O To a sealed tube was added 19 (55 mg, 0.136 mmol), indole-4-boronic acid (55 mg, 0.34 mmol), dichloro-bis(triphenylphosphine)palladium (II) (19 mg, 0.027 mmol) and Na₂CO₃ (29 mg, 0.27 mmol) followed by dioxane (3.5 mL) and water (1.4 mL) under Ar(g). The tube was heated to 88° C. for 18 h whereupon it was cooled to rt and diluted with EtOAc (45 mL) and 50% saturated brine (7 mL). The organic layer was separated and the aqueous layer extracted with EtOAc (2×10 mL). The combined organic layers were then dried (MgSO₄) and concentrated in vacuo. Purification by flash column chromatography on silica (eluant 1-3% MeOH/CH₂Cl₂) furnished O (30 mg, 0.06 mmol, 45%) as a brown solid.

¹H NMR (300MHz, CDCl₃) δ$_H$: 8.62 (d, J=2.2Hz, 1H), 8.55 (d, J=2.2Hz, 1H), 8.34 (br. s., 1H), 8.24 (d, J=7.0 Hz, 1H), 7.59-7.68 (m, 1H), 7.54 (d, J=8.1Hz, 1H), 7.31-7.41 (m, 2H), 4.57-4.88 (m, 1H), 4.20-4.34 (m, 4H), 3.89-4.00 (m, 4H), 3.72 (s, 2H), 2.57-2.74 (m, 2H), 2.39-2.54 (m, 2H), 1.81-2.04 (m, 4H).

LCMS (ES⁺) 487 (100%, [M+H]⁺).

Example P 8-(4,4-Difluoro-piperidin-1-ylmethyl)-2-(1H-indol-4-yl)-4-morpholin-4-yl-pyrido[3',2':4,5]furo[3,2-d]pyrimidine

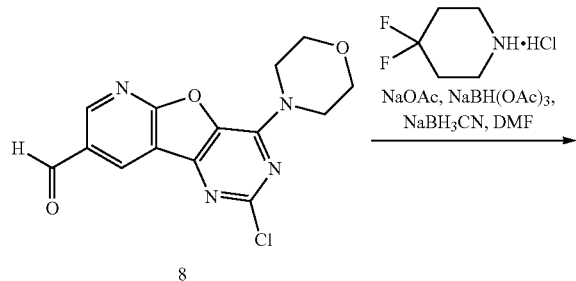

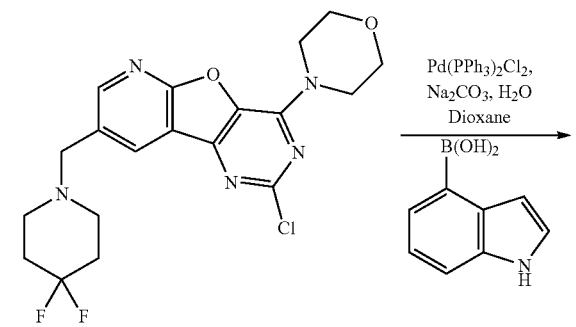

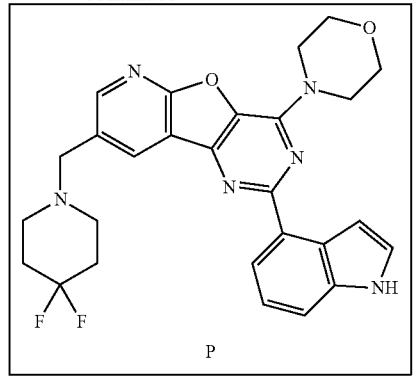

i. 8-(4,4-Difluoro-piperidin-1-ylmethyl)-2-(1H-indol-4-yl)-4-morpholin-4-yl-pyrido[3',2':4,5]furo[3,2-d]pyrimidine, 20

To compound 8 (as per Example H above) (80 mg, 0.25 mmol) in dry DMF (12 mL) was added 4,4-difluoropiperidine hydrochloride (79 mg, 0.5 mmol) and NaOAc (41 mg, 0.5 mmol) under Ar(g). After 20 minutes NaBH(OAc)₃ (106 mg, 0.5 mmol) and NaBH₃CN (16 mg, 0.25 mmol) were added and the suspension was stirred for 16 h. The DMF was then removed in vacuo, EtOAc (45 mL) was added along with 50% saturated brine (7 mL), the layers separated, extracted with EtOAc (2×15 mL), dried (MgSO₄) and concentrated in vacuo. Purification by flash column chromatography on silica (eluant 1-2% MeOH/CH₂Cl₂) furnished 20 (41 mg, 0.097 mmol, 39%) as a white solid.

¹H NMR (300MHz, CDCl₃) δ$_H$: 8.55 (d, J=2.0Hz, 1H), 8.51 (d, J=2.0Hz, 1H), 4.08-4.23 (m, 4H), 3.82-3.93 (m, 4H), 3.74 (s, 2H), 2.54-2.66 (m, 4H), 1.92-2.12 (m, 4H).

LCMS (ES⁺) 424 (100%, [M+H]⁺).

ii. [2-(1H-Indol-4-yl)-4-morpholin-4-yl-pyrido[3',2':4,5]furo[3,2-d]pyrimidin-8-ylmethyl]-(2-methoxy-ethyl)-methyl-amine, N To a sealed tube was added 20 (41 mg, 0.097 mmol), indole-4-boronic acid (39 mg, 0.24 mmol), dichloro-bis(triphenylphosphine)palladium (II) (13.6 mg, 0.02 mmol) and Na₂CO₃ (21 mg, 0.19 mmol) followed by dioxane (3.5 mL) and water (1.4 mL) under Ar(g). The tube was heated to 88° C. for 18 h, and the reaction mixture was then cooled to rt, and diluted with EtOAc (45 mL) and 50% saturated brine (7 mL). The organic layer was separated and the aqueous layer extracted with EtOAc (2×10 mL). The combined organic layers were then dried (MgSO₄) and concentrated in vacua. Purification by flash column chromatography on silica (eluant 0.5-2% MeOH/CH₂Cl₂) furnished P (7.4 mg, 0.015 mmol, 15%) as a white solid.

¹H NMR (300MHz, CDCl₃) δ$_H$: 8.61 (d, J=2.3Hz, 1H), 8.54 (d, J=2.3Hz, 1H), 8.38 (br. s., 1H), 8.24 (dd, J=7.5, 0.8Hz, 1H), 7.58-7.65 (m, 1H), 7.53 (d, J=7.9Hz, 1H), 7.37-7.40 (m, 1H), 7.34 (t, J=7.9Hz, 1H), 4.21-4.32 (m, 4H), 3.91-3.99 (m, 4H), 3.76 (s, 2H), 2.56-2.70 (m, 4H), 1.95-2.14 (m, 4H).

LCMS (ES⁺) 505 (100%, [M+H]⁺).

Example Q 2-(1H-Indol-4-yl)-8-[4-(2-methoxy-ethyl)-piperazin-1-ylmethyl]-4-morpholin-4-yl-pyrido[3',2':4,5]furo[3,2-d]pyrimidine

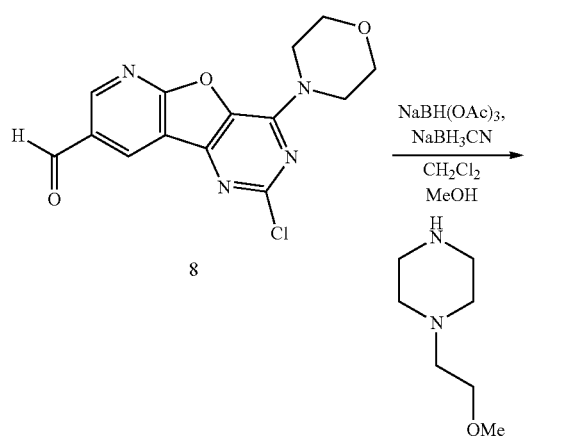

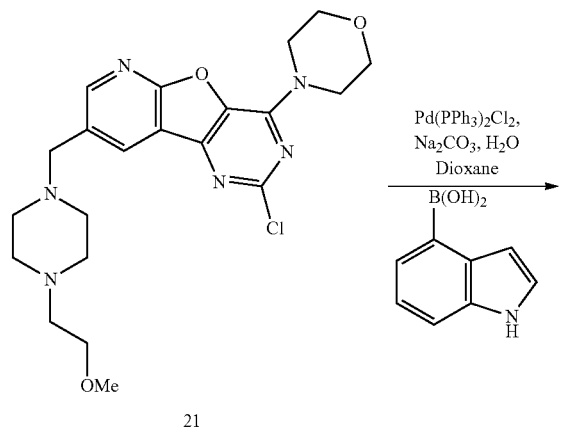

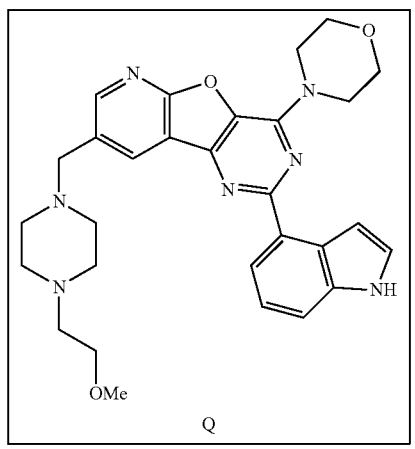

Q i. 2-Chloro-8-[4-(2-methoxy-ethyl)-piperazin-1-ylmethyl]-4-morpholin-4-yl-pyrido[3',2':4,5]furo[3,2-d]pyrimidine, 21

To compound 8 (as per Example H above) (22.2 mg, 0.070 mmol) in dry $CH_2Cl_2$/MeOH (5 mL/2 mL) was added 1-(2-methoxyethyl) piperazine (13 μL, 0.093 mmol) and the reaction was stirred for 1 h. NaBH(OAc)$_3$ (45.8 mg, 0.022 mmol) was then added, followed by NaBH$_3$CN (4.4 mg, 0.070 mmol), and the reaction mixture was stirred for 48 h. EtOAc (30 mL) was added along with water/saturated brine (10 mL/5 mL); the layers were separated, extracted with EtOAc (2×30 mL), dried (MgSO$_4$) and concentrated in vacuo. Purification by flash column chromatography on silica (eluant 2:98-6:94 MeOH/CH$_2$Cl$_2$) furnished 21 (10 mg, 0.022 mmol, 32%) as a white solid.

$^1$H NMR (300MHz, 9.5:0.5 CDCl$_3$/CD$_3$OD) $\delta_H$ 8.53 (d, J=1.9Hz, 1H), 8.47-8.52 (m, 1H), 4.14 (br. s., 4H), 3.83-3.93 (m, 4H), 3.68 (s, 2H), 3.48-3.57 (m, 2H), 3.34 (s, 3H), 2.47-2.66 (m, 10H). MS (ES$^+$) 447.2 (100%, [M+H]$^+$).

ii. 2-(1H-Indol-4-yl)-8[4-(2-methoxy-ethyl)-piperazin-1-ylmethyl]-4-morpholin-4-yl-pyrido[3',2':4,5]furo[3,2-d]pyrimidine, Q To indole-4-boronic acid (8.6 mg, 0.053 mmol), dichlorobis(triphenylphosphine)palladium (II) (3.0 mg, 0.0043 mmol) and sodium carbonate (4.7 mg, 0.045 mmol) was added compound 21 (10.0 mg, 0.022 mmol) dissolved in dioxane/water (2 mL/0.8 mL). The reaction was then heated in a sealed tube at 88° C. for 16 h, and was subsequently cooled to rt; it was then partitioned between EtOAc/water (30 mL/5 mL), the layers separated, extracted with EtOAc (2×30 mL), dried (MgSO$_4$) and concentrated in vacuo. Purification by flash column chromatography on silica (eluant 0:1-2:98 MeOH/CH$_2$Cl$_2$) furnished Q (1.09 mg, 0.0021 mol, 9%) as a white solid.

LCMS (ES$^+$) 528.3 (100%, [M−H]$^+$).

Example R

3-{4-[2-(1H-Indol-4-yl)-4-morpholin-4-yl-pyrido[3',2':4,5]furo[3,2-d]pyrimidin-8-ylmethyl]-piperazin-1-yl}-propionitrile

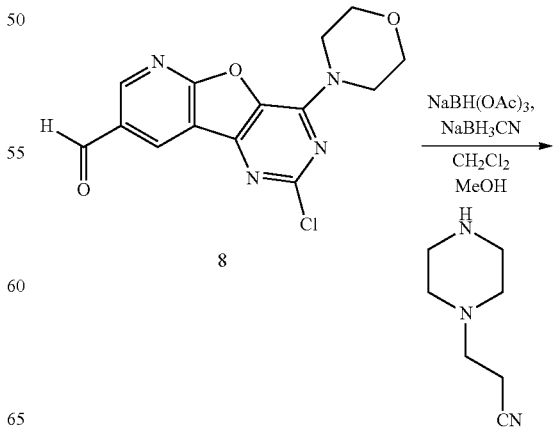

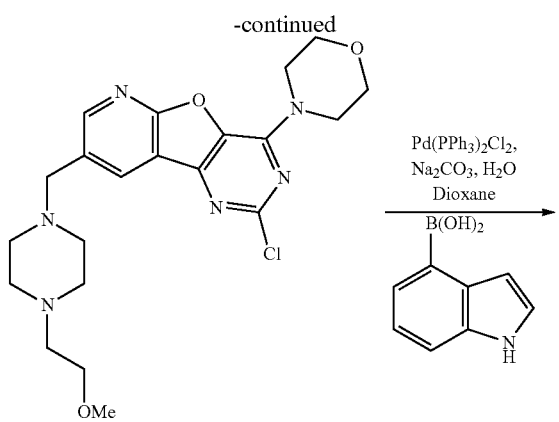

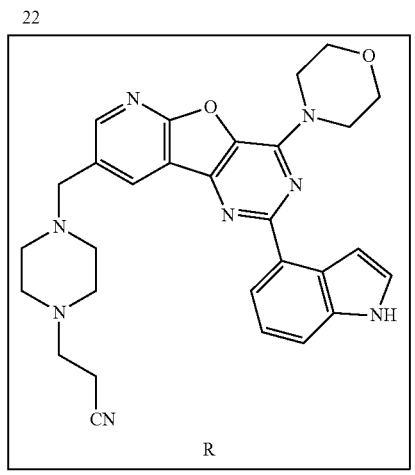

i. 3-[4-(2-Chloro-4-morpholin-4-yl-pyrido[3',2':4,5]furo[3,2-d]pyrimidin-8-ylmethyl)-piperazin-1-yl]-propionitrile, 22

To compound 8 (as per Example H above) (24.2 mg, 0.076 mmol) in dry CH$_2$Cl$_2$/MeOH (5 mL/2 mL) was added 3-(1-piperazinyl) propionitrile (15 μL, 0.11 mmol) and the reaction mixture was stirred for 15 mins. NaBH(OAc)$_3$ (47.8 mg, 0.023 mmol) was then added, and the resulting mixture was stirred for 17 h. NaBH$_3$CN (4.8 mg, 0.076 mmol) was added, and following additional stirring for a further 5 h, the reaction mixture was partitioned between EtOAc/water/saturated brine (30 mL/10 mL/5 mL), the layers separated, extracted with EtOAc (2×30 mL), dried (MgSO$_4$) and concentrated in vacuo. Purification using an SCX-2 column with MeOH/CH$_2$Cl$_2$ (1:9-1:1-1:1+0.2M NH$_3$ in MeOH) followed by flash column chromatography on silica (eluant 1:9 MeOH/CH$_2$Cl$_2$) furnished 22 (15.1 mg, 0.034 mmol, 45%) as a white solid.

$^1$H NMR (400MHz, 9:1 CDCl$_3$/CD$_3$OD) δ$_H$ 8.43 (d, J=2.0Hz, 1H), 8.38 (d, J=2.0Hz, 1H), 4.04 (br. s., 4H), 3.76 (t, 4H, J=5.0Hz), 3.60 (s, 2H), 2.57-2.64 (m, 2H), 2.40-2.51 (m, 10H).

MS (ES$^+$) 442.1 (100%, [M+H]$^+$).

ii. 3-{4-[2-(1H-Indol-4-yl)-4-morpholin-4-yl-pyrido[3',2':4,5]furo[3,2-d]pyrimidin-8-ylmethyl]-piperazin-1-yl}-propionitrile, R To indole-4-boronic acid (14.6 mg, 0.091 mmol), dichlorobis(triphenylphosphine)palladium (II) (4.7 mg, 0.0066 mmol) and sodium carbonate (7.5 mg, 0.071 mmol) was added 22 (15.1 mg, 0.034 mmol) dissolved in dioxane/water (2 mL/0.8 mL). The reaction mixture was heated in a sealed tube at 88° C. for 16 h, was subsequently cooled to rt, and was then partitioned between EtOAc/water (30 mL/5 mL). The layers were separated, extracted with EtOAc (2×30 mL), dried (MgSO$_4$) and concentrated in vacuo. Purification by flash column chromatography on silica (eluant 2:98-4:96-6:94) MeOH/CH$_2$Cl$_2$) furnished R (6.8 mg, 0.013 mol, 38%) as a white solid.

$^1$H NMR (400MHz, CDCl$_3$) δ$_H$ 8.60 (s, 1H), 8.54 (s, 1H), 8.40 (br. s., 1H), 8.24 (dd. J=7.5, 1.0Hz, 1H), 7.60-7.63 (m, 1H), 7.53 (d, J=8.0 Hz, 1H), 7.38 (br. s., 1H), 7.34 (t, J=7.8Hz, 1H), 4.26 (t, J=4.3Hz, 4H), 3.94 (t, J=4.5 Hz, 4H), 3.72 (s, 2H), 2.69-2.75 (m, 2H), 2.48-2.65 (m, 10H).

MS (ES$^+$) 523.2 (100%, [M−H]$^+$).

Example S

Cyclopropyl-[2-(1H-indol-4-yl)-4-morpholin-4-yl-pyrido[3',2':4,5]furo[3,2-d]pyrimidin-8-ylmethyl]-methyl-amine

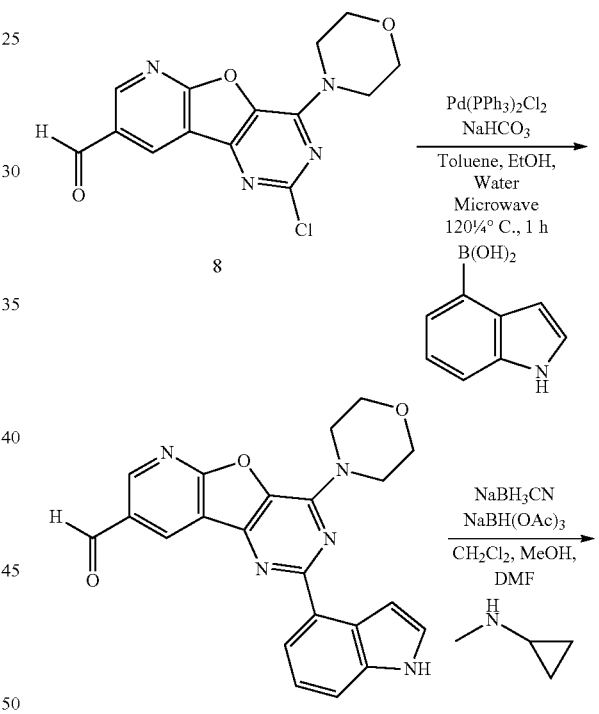

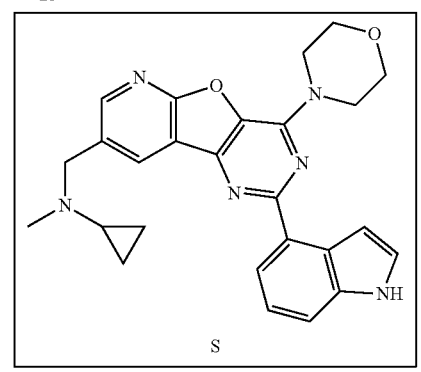

i. 2-(1H-Indol-4-yl)-4-morpholin-4-yl-pyrido[3',2':4,5]furo[3,2-d]pyrimidine-8-carbaldehyde, 23

To compound 8 (as per Example H above) (40 mg, 0.13 mmol, 1 eq), indole-4-boronic acid (61 mg, 0.38 mmol, 3 eq) and PdCl$_2$(PPh$_3$)$_2$ (18.0 mg, 0.03 mmol, 20 mol %) in a mixture of toluene (2.5 mL), ethanol (1.5 mL) and H$_2$O (0.8 mL) was added NaHCO$_3$ (32 mg, 0.38 mmol, 3 eq) under Ar(g). The reaction mixture was heated in a microwave for 1 h at 120° C. Once cooled down, the mixture was partitioned with H$_2$O (10 mL) and extracted with CH$_2$Cl$_2$ (2×10 mL) and EtOAc (2×10 mL). The combined organic extracts were dried over MgSO$_4$ and the solvent was removed in vacuo. The resulting residue was further purified by silica gel column chromatography with CH$_2$Cl$_2$/MeOH (1:0-19:1) to yield the product, 23, as a pale yellow solid (33.0 mg, 65%).

$^1$H NMR (300MHz, DMSO-d$_6$) δ$_H$: 11.27 (br. s, 1H), 10.26 (s, 1H), 9.16 (d, J=2.3Hz, 1H), 9.11 (d, J=2.3Hz, 1H), 8.18 (d, J=7.5Hz, 1H), 7.58-7.67 (m, 2H), 7.49 (t, J=2.8Hz, 1H), 7.23 (t, J=7.7Hz, 1H), 4.08-4.16 (m, 4H), 3.83-3.90 (m, 4H).

MS (ES$^+$) 432.0 (100%, [M+H+MeOH]$^+$).

ii. Cyclopropyl-[2-(1H-indol-4-yl)-4-morpholin-4-yl-pyrido[3',2':4,5]furo[3,2-d]pyrimidin-8-ylmethyl]-methyl-amine, S To a solution of compound 23 (19 m$_0$, 0.048 mmol, 1 eq), NaBH$_3$CN (6.0 mg, 0.096 mmol. 2 eq), NaBH(OAc)$_3$ (31 mg, 0.144 mmol, 3 eq) in a mixture of anhydrous CH$_2$Cl$_2$ (2 mL), MeOH (2 mL) and DMF (0.5 mL) was added cyclopropyl-methyl-amine (19 µL, 019 mmol, 4 eq) under Ar(g). The reaction mixture was stirred at rt overnight, and the solvents were removed in vacuo. The resulting residue was then partitioned with H$_2$O (10 mL) and extracted with CH$_2$Cl$_2$ (3×10 mL) and EtOAc (2×10 mL). The combined organic extracts were dried over MgSO$_4$ and the solvent was removed in vacuo. The residue was further purified by silica gel column chromatography with CH$_2$Cl$_2$/MeOH (1:0-24:1) to furnish the product, S, as a white solid (9.56 mg, 44%).

$^1$H NMR (300MHz, CDCl$_3$) δ$_H$: 8.55 (d, J=2.3Hz, 1H), 8.50 (d, J=2.3Hz, 1H), 8.33 (br. s., 1H), 8.23 (dd, J=7.5, 0.8Hz, 1H), 7.58-7.63 (m, 1H), 7.50-7.56 (m, 1H), 7.37-7.40 (m, 1H), 7.30-7.37 (m, 1H), 4.22-4.30 (m, 4H), 3.91-3.98 (m, 4H), 3.89 (s, 2H), 2.33 (s, 2H), 1.76-1.84 (m, 1H), 0.43-0.58 (m, 4H).

MS (ES$^+$) 455.1 (100%, [M+H]$^+$).

Example T

Cyclopropylmethyl-[2-(1H-indol-4-yl)-4-morpholin-4-yl-pyrido[3',2':4,5]furo[3,2-d]pyrimidin-8-ylmethyl]-methyl-amine

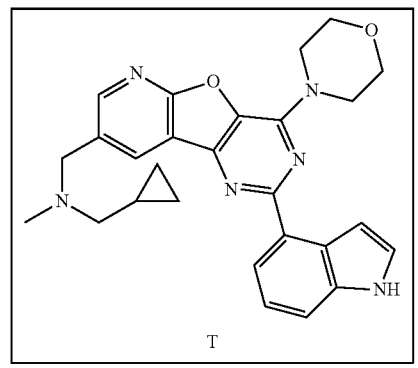

T

To a solution of compound 23 (as per Example S above) (19 mg, 0.048 mmol, leg), NaBH$_3$CN (6.0 mg, 0.096 mmol. 2 eq), NaBH(OAc)$_3$ (31 mg, 0.144 mmol, 3 eq), NaOAc (15.7 mg, 0.19 mmol, 4 eq) in a mixture of anhydrous CH$_2$Cl$_2$ (2 mL), MeOH (2 mL) and DMF (0.5 mL) was added cyclopropylmethyl-methyl-amine hydrochloride (23 mg, 0.19 mmol, 4 eq) under Ar(g). The reaction mixture was stirred at rt overnight. Solvents were removed in vacuo. Then, the residue was partitioned with H$_2$O (10 mL) and extracted with CH$_2$Cl$_2$ (3×10 mL) and EtOAc (2×10 mL). The combined organic extracts were dried over MgSO$_4$ and the solvent was removed in vacuo. The residue was further purified by silica gel column chromatography with CH$_2$Cl$_2$/MeOH (1:0-47:3) to yield the product, T, as a white solid (8.35 mg, 37%).

$^1$H NMR (300MHz, CDCl$_3$+10% CD$_3$OD) δ$_H$: 8.57 (d, J=2.3Hz, 1H), 8.49 (d, J=2.3Hz, 1H), 8.05 (dd, J=7.5, 1.1Hz, 1H), 7.47 (d, J=8.3Hz, 1H), 7.37 (dd, J=3.4, 0.8Hz, 1H), 7.30 (d, J=3.4Hz, 1H), 7.19-7.26 (m, 1H), 4.16-4.22 (m, 4H), 3.84-3.90 (m, 4H), 3.75 (s, 2H), 2.32 (d, J=6.8 Hz, 2H), 2.29 (s, 3H), 0.46-0.54 (m, 2H), 0.04-0.12 (m, 2H).

MS (ES$^+$) 469.1 (100%, [M−H]$^+$).

Example U

8-Azetidin-1-ylmethyl-2-(1H-indol-4-yl)-4-morpholin-4-yl-pyrido[3',2':4,5]furo[3,2-d]pyrimidine

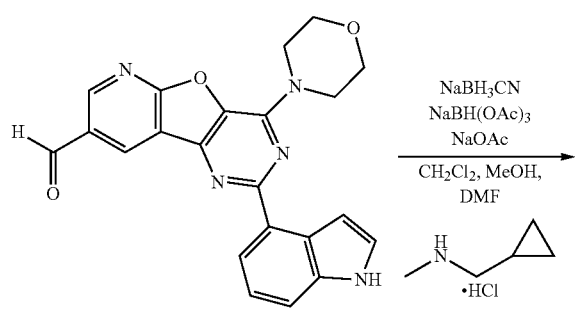

23

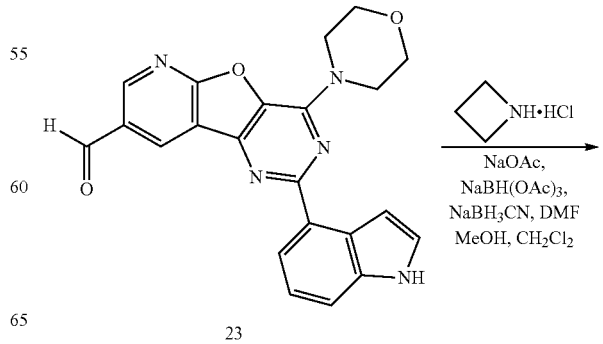

23

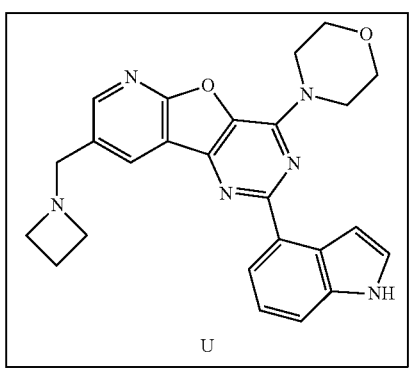

To compound 23 (as per Example S above) (17 mg, 0.04 mmol) in a mixture of dry DMF (2 mL), CH$_2$Cl$_2$ (0.5 mL) and MeOH (0.2 mL) was added azetidine hydrochloride (16 mg, 0.17 mmol) and NaOAc (14 mg, 0.17 mnnol) under Ar(g). After 5 minutes NaBH(OAc)$_3$ (27 m0, 0.13 mmol) and NaBH$_3$CN (5.4 mg, 0.09 mmol) were added and the reaction mixture was stirred for 16 h. EtOAc (45 mL) was added along with 50% saturated brine (5 mL); the layers were separated, extracted with EtOAc (3×10 mL), dried (MgSO$_4$) and concentrated in vacuo. Purification by flash column chromatography on silica (eluant 2-8% MeOH/CH$_2$Cl$_2$) furnished U (5.4 mg, 0.012 mmol, 28%) as an off-white solid.

$^1$H NMR (300MHz, 9:1 CDCl$_3$/CD$_3$OD) $\delta_H$:8.52 (d, J=2.3Hz, 1H), 8.43 (d, J=2.3Hz, 1H), 8.02 (dd, J=7.5, 1.1Hz, 1H), 7.47 (d, J=7.9Hz, 1H), 7.34 (dd, J=3.4, 0.8Hz, 1H), 7.29 (d, J=3.0 Hz, 1H), 7.22 (t, J=7.8 Hz, 1H), 4.15-4.21 (m, 4H), 3.83-3.89 (m, 4H), 3.73 (s, 2H), 3.20-3.33 (m, 4H), 2.01-2.15 (m, 2H).

LCMS (ES$^+$) 441 (100%, [M+H]$^+$).

Biological Data

1) PI3K Isoform Biochemical Data

| Compound | IC$_{50}$ (nM) PI3K | | | |
|---|---|---|---|---|
| | p110α | p110β | p110δ | p110γ |
| A | 54 | 137 | 15 | 873 |
| B | 159 | 19 | 6 | 317 |
| D | 104 | 57 | 33 | 103 |
| E | 88 | 69 | 7 | 627 |
| F | 127 | 109 | 6 | 269 |
| G | 223 | 83 | 5 | 1655 |
| H | 398 | 63 | 6 | 213 |
| I | 508 | 503 | 10 | 4946 |
| J | 680 | 277 | 26 | 1039 |
| K | 355 | 64 | 6 | 2612 |
| L | 604 | 111 | 21 | 1820 |
| M | 96 | 25 | 10 | 219 |
| R | 597 | 131 | 22 | 2536 |

2) Anti-Inflammatory Activity: Inhibition of the Production of Pro-Inflammatory Cytokines from Stimulated Human Peripheral Blood Mononuclear Cells (hPBMCs)

Compounds were tested at a concentration of 1 uM for cytokine release inhibition in hPBMCs stimulated with LPS (TNFα), PHA (IFNγ) and anti-CD3 (IL-17A, IL-17F, IL-21, IL-23):

| Compound | % Inhibition of Proinflammatory Cytokine Production at 1 uM | | | | | |
|---|---|---|---|---|---|---|
| | TNFα | IFNγ | IL-17A | IL-17F | IL-21 | IL-23 |
| B | 26 | 73 | 99 | 96 | 96 | 94 |
| F | 74 | 67 | 77 | 74 | 82 | 93 |
| H | 75 | 87 | 99 | 96 | 96 | 93 |
| I | 61 | 80 | 95 | 95 | 96 | 90 |

3) In Vitro Inhibition of Rheumatoid Arthritis Synovial Fibroblast (RASF) Proliferation

| Compound | IC$_{50}$ (nM) RASF Proliferation |
|---|---|
| A | 1347 |
| B | 817 |
| F | 2237 |
| H | 1901 |
| I | 5722 |
| K | 3020 |
| M | 1610 |

4) In Vitro Inhibition of Tumour Cell Proliferation

| Compound | IC$_{50}$ (nM) | | |
|---|---|---|---|
| | PC3 (Prostate Tumour) | MCF7 (Breast Tumour) | A549 (Lung Tumour) |
| A | 3013 | 331 | 151 |
| B | 1339 | 145 | 229 |
| F | 7294 | 215 | 1152 |
| G | 3770 | 127 | 186 |
| H | 3030 | 165 | 466 |
| K | 3336 | 352 | 682 |
| L | 3244 | 119 | 1605 |

The invention claimed is:
1. A compound represented by formula I:

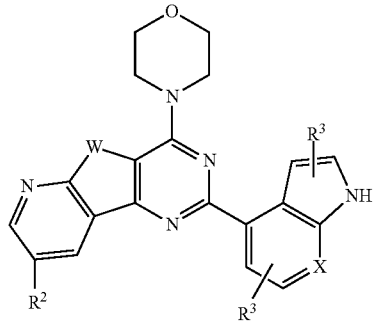

or a pharmaceutically acceptable salt thereof, wherein:
W is O;
X is CH;
R$^2$ is (LQ)$_m$Y;
m is 1;
L is C$_1$alkylene;
Q is selected from the group consisting of: heteroarylene, —NR$^3$—, —C(O)—, —NR$^4$R$^5$—, and —C(O)NR$^4$R$^5$, where R$^4$ and R$^5$ together with the nitrogen to which they are attached form a 5 to 7-membered heterocycle linker;
Y is selected from the group consisting of: H, C$_1$-C$_{10}$ alkyl, C$_3$-C$_{10}$ cycloalkyl, —OR$^3$, —N(R$^3$)$_2$, —SO$_2$—R$^3$, —SO$_2$—N(R$^3$)$_2$, halogen, —CN, and —C(halogen)$_b$R$^3{}_{(3-b)}$,
b is from 1 to 3; and
R$^3$ is independently selected for each occurrence from H or C$_1$-C$_{10}$ alkyl.

2. The compound according to claim 1, wherein both of the R³ groups that are attached to the 6,5-ring system in formula I are H.

3. The compound according to claim 1, wherein Q is —NR⁴R⁵ wherein R⁴ and R⁵ together with the nitrogen to which they are attached form a 5 to 7-membered heterocycle linker having an additional heteroatom O; and Y is H.

4. A compound selected from the structures shown below:

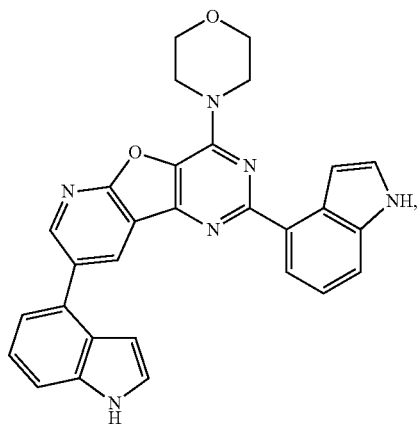
E

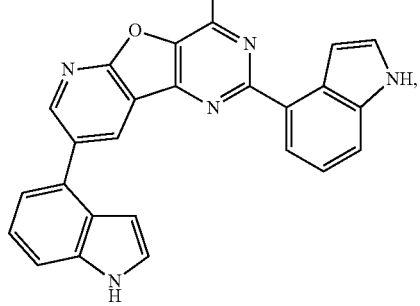
F

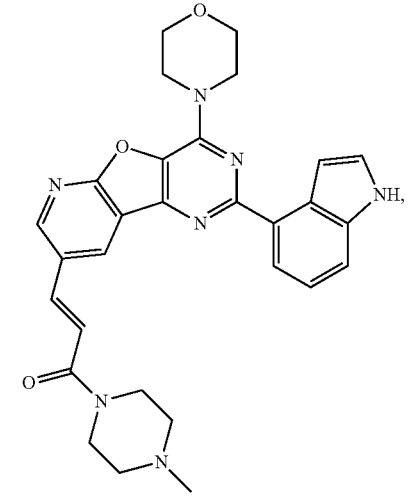
G

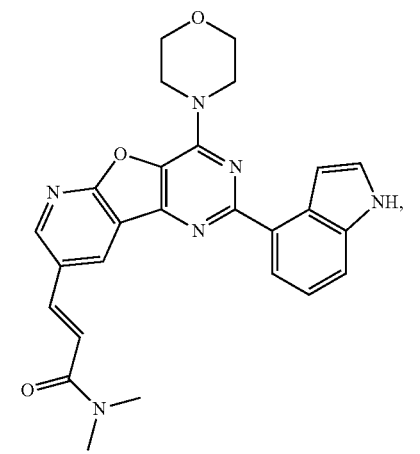

-continued

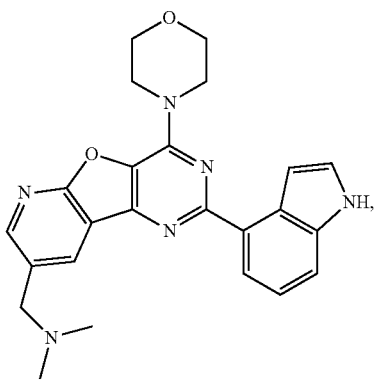
H

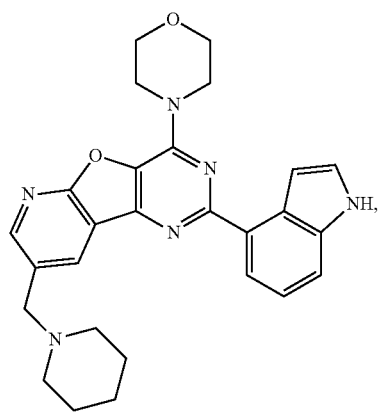
I

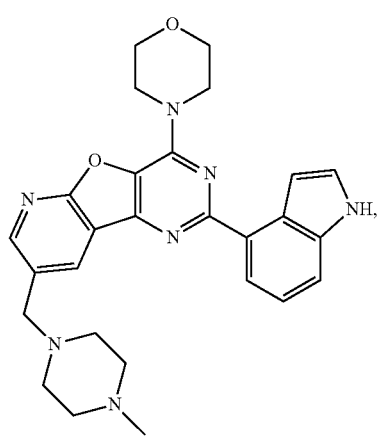
J

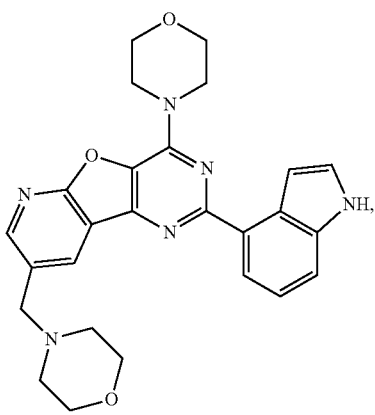
K

53
-continued
L
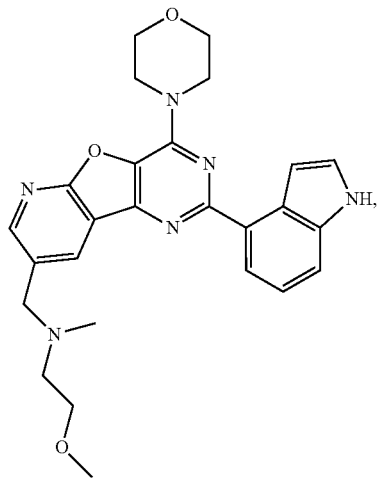
M
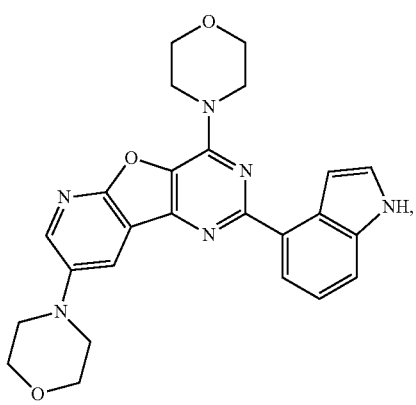
O
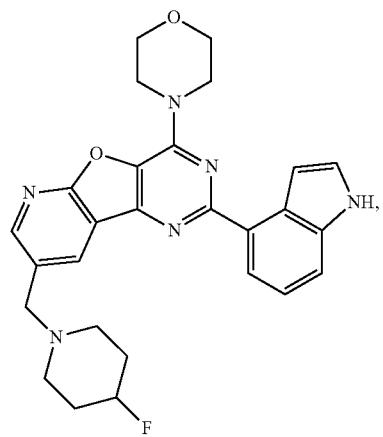
54
-continued
P
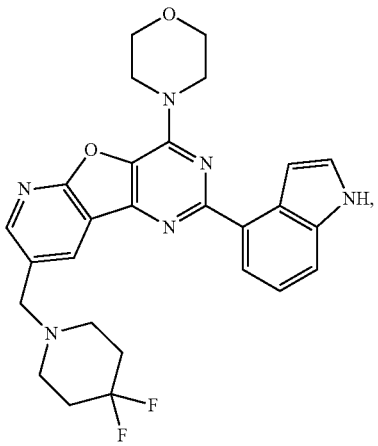
Q
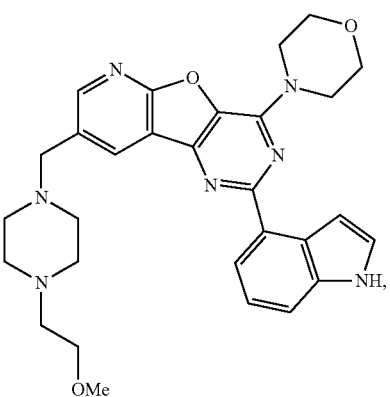
R
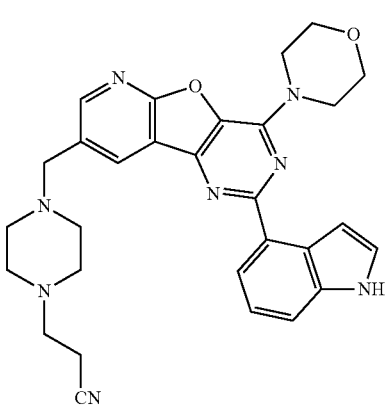

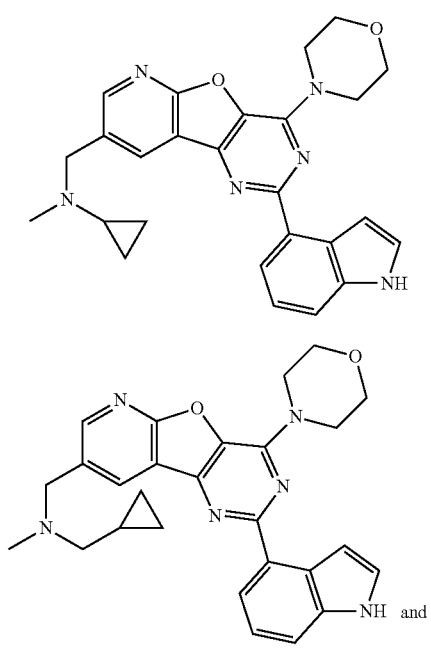
and
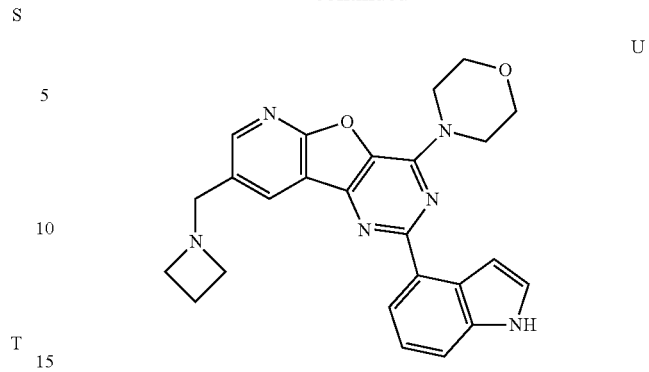
or a pharmaceutically acceptable salt thereof.
5. A pharmaceutical composition comprising a compound according to claim 1, and a pharmaceutically acceptable excipient.
6. The compound according to claim 1, wherein Q is selected from —NR$^3$— and —NR$^4$R$^5$—.
* * * * *